United States Patent
Kojoh et al.

(10) Patent No.: US 10,865,247 B2
(45) Date of Patent: Dec. 15, 2020

(54) ANTI-HUMAN CD69 ANTIBODY, AND USE THEREOF FOR MEDICAL PURPOSES

(71) Applicants: GeneFrontier Corporation, Kashiwa (JP); National University Corporation Chiba University, Chiba (JP)

(72) Inventors: Kanehisa Kojoh, Kashiwa (JP); Akira Miyakoshi, Kashiwa (JP); Shizue Katoh, Kashiwa (JP); Kumiko Tsuihiji, Kashiwa (JP); Yuki Hayami, Kashiwa (JP); Mikiko Nakamura, Kashiwa (JP); Toshinori Nakayama, Chiba (JP); Chiaki Iwamura, Chiba (JP)

(73) Assignees: GeneFrontier Corporation, Chiba (JP); National University Corporation Chiba University, Chiba (JP)

( * ) Notice: Subject to any disclaimer, the term of this patent is extended or adjusted under 35 U.S.C. 154(b) by 0 days.

(21) Appl. No.: 16/796,481

(22) Filed: Feb. 20, 2020

(65) Prior Publication Data
US 2020/0199235 A1    Jun. 25, 2020

Related U.S. Application Data

(63) Continuation of application No. 16/153,449, filed on Oct. 5, 2018, now abandoned, which is a continuation of application No. 14/396,521, filed as application No. PCT/JP2013/061918 on Apr. 23, 2013, now abandoned.

(30) Foreign Application Priority Data

Apr. 23, 2012 (JP) .................................. 2012-098243

(51) Int. Cl.
*C07K 16/28*    (2006.01)
*A61K 39/395*   (2006.01)
*A61K 39/00*    (2006.01)

(52) U.S. Cl.
CPC .... *C07K 16/2851* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/565* (2013.01); *C07K 2317/92* (2013.01)

(58) Field of Classification Search
CPC ............ C07K 16/2851; C07K 16/2896; C07K 2317/565; C07K 2317/21; C07K 2317/33; C07K 2317/34; A61K 2039/505
See application file for complete search history.

(56) References Cited

PUBLICATIONS

Mariuzza, R.A. et al. 'The Structural Basis of Antigen-Antibody Recognition' Annu. Rev. Biophys. Biphys. Chem. 16:139-159, 1987.*
Rudikoff et al. "Single Amino Acid Substitution Altering Antigen-Binding Specificity" PNAS. 79:1979-1983, 1982.*
Rader et al. PNAS. 95:8910-8915, 1998.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
MacCallum et al. "Antibody-antigen interactions: contact analysis and binding site topography", J. Mol. Biol. vol. 262, pp. 732-745, 1996.*
De Pascalis et al. "Grafting of abbreviated complementarity determining regions containing specificity determining residues essential for ligand contact to engineer a less immunogenic humanzied monoclonal antibody", J. Immunol. 169, pp. 3076-3084, 2002.*

* cited by examiner

*Primary Examiner* — Phuong Huynh
(74) *Attorney, Agent, or Firm* — Osha Bergman Watanabe & Burton LLP

(57) ABSTRACT

The present invention provides an antibody that specifically binds to human CD69, has an activity to suppress allergic inflammation, and has cross-reactivity with mouse CD69. In addition, the present invention provides an antibody having high binding affinity for human CD69 and an activity to suppress allergic inflammations. The antibody of the present invention can be a human antibody.

12 Claims, 5 Drawing Sheets

Specification includes a Sequence Listing.

Eos: eosinophil, Neu: neutrophil, Lym: lymphocyte, M phage: macrophage

Human CD69

Sample: PBMC from normal human subject
Stimulation: PMA (100ng/ml, 4h)

Mouse CD69

Sample: Splenocytes from WT or CD69KO mice (BALB/c)
Stimulation: PMA (100ng/ml, 4h)

Eos: eosinophil, Neu: neutrophil, Lym: lymphocyte, M phage: macrophage

Fig. 6

```
Mouse CD69    MDSENCSITENSSSHLERGQKDHGTSIHFEKHHEGSIQVSIPWAVLIVVLITSLIIALIA    60
              |.||||..||||  | |.||....|| ||...||||.||..  ||. ||.|| ||||||
Human CD69    MSSENCFVAENSSLHPESGQENDATSPHFSTRHEGSFQVPVLCAVMNVVFITILIIALIA    60

Mouse CD69    LNVGKYNCPGLYEKLESSDHHVATCKNEWISYKRTCYFFSTTTKSWALAQRSCSEDAATL   120
              |.||.|||||  |.   .|| ||..|...|..|.|.|||.||...|.  ||..|||..|||
Human CD69    LSVGQYNCPGQYTFSMPSDSHVSSCSEDWVGYQRKCYFISTVKRSWTSAQNACSEHGATL   120

Mouse CD69    AVIDSEKDMTFLKRYSGELEHWIGLKNEANQTWKWANGKEFNSWFNLTGSGRCVSVNHKN   180
              |||||||||.|||||.|    |||.|||.|....|||.||||||.|||.|||..||.....
Human CD69    AVIDSEKDMNFLKRYAGREEHWVGLKKEPGHPWKWSNGKEFNNWFNVTGSDKCVFLKNTE   180

Mouse CD69    VTAVDCEANFHWVCSKP    197
              |....|| |..|.|.||
Human CD69    VSSMECEKNLYWICNKP    197
```

ANTI-HUMAN CD69 ANTIBODY, AND USE THEREOF FOR MEDICAL PURPOSES

CROSS-REFERENCE TO RELATED APPLICATIONS

This patent application is a continuation of U.S. patent application Ser. No. 16/153,449, filed on Oct. 5, 2018, which is a continuation of U.S. patent application Ser. No. 14/396,521, filed on Oct. 23, 2014, which is the U.S. national phase of International Patent Application No. PCT/JP2013/061918, filed on Apr. 23, 2013, which claims the benefit of Japanese Patent Application No. 2012-098243, filed on Apr. 23, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith.

TECHNICAL FIELD

The present invention relates to an anti-human CD69 antibody, and pharmaceutical use thereof.

BACKGROUND ART

CD69 is a type II transmembrane protein belonging to the C-type lectin family. Since the expression of CD69 increases within a few hours after stimulation of T cells and B cells, it is widely used as an early activation marker molecule to be an index of lymphocyte activation (non-patent document 1). In addition, the expression is also observed in T cells under so selection during differentiation in thymus (non-patent documents 2 and 3). While CD69 is assumed to have a function as a coreceptor to potentiate signal transduction from an antigen receptor, the detail is unknown. Its ligand has not been identified to date. It is constitutively expressed in platelet, and the expression is also observed in activated neutrophils, eosinophils and the like. Therefore, it is assumed to play a role in the expression of function in platelets and topical inflammation reactions. Also, it has been clarified that CD69 on the neutrophil plays an important role in the onset of arthritis (non-patent document 4). Furthermore, it has been reported that CD69 controls allergic airway inflammation, and an antibody to mouse CD69 inhibits allergic airway inflammation (non-patent document 5). It has also been reported that COPD induced by cigarette smoke and lung fibrogenesis induced by bleomycin are attenuated in CD69 deficient mouse (non-patent document 6 and 7). Therefore, application of an antibody to CD69 to the prophylaxis or treatment of such allergic diseases and inflammatory diseases is expected. However, since the ligand for CD69 is unknown, a method for efficiently evaluating in vitro a pharmacological effect of an antibody to human CD69 is not available. Moreover, since existing antibodies to human CD69 do not cross-react with non-human CD69, evaluation of a pharmacological effect of the existing antibodies in vivo is substantially impossible, and even whether or not these antibodies afford a useful pharmacological effect is not clear. As described above, since a satisfactory method for evaluation of a pharmacological effect of an anti-human CD69 antibody does not exist, the development of an anti-human CD69 antibody applicable to the prophylaxis or treatment of allergic diseases and inflammatory diseases is delayed far behind.

The phage display method is one of the display techniques that have realized an in vitro high-speed selection by forming a one-to-one correspondence in the form of phage particle between a functional peptide or protein and a DNA encoding same. This phage display method has been applied to antibody selection, and antibodies obtained by this method have been developed as medicaments (non-patent document 8). Furthermore, a method of obtaining a specific antibody by combining a human artificial antibody library and a phage display method has been established, and such methods have been practicalized by plural companies, as evidenced by HuCAL (Human Combinatorial Antibody Library) of MorphoSys.

DOCUMENT LIST

Non-Patent Documents non-patent document 1: Testi, R. et al. Immunol. Today 15: 479-483, 1994.
non-patent document 2: Yamashita, T. et al. Int. Immunol. 5: 1139-1150, 1993.
non-patent document 3: Nakayama, T. et al. J. Immunol. 168: 87-94, 2002.
non-patent document 4: Murata, K. et al. Int. Immunol. 15: 987-992, 2003.
non-patent document 5: Miki-Hosokawa, T. et al. J. Immunol. 183: 8203-8215, 2009.
non-patent document. 6: Tsuyusaki, J. et al. J. Recept. Signal Transduct. Res. 31: 434-439, 2011.
non-patent document 7: Yamauchi, K. et al. Respir. Res. 12: 131, 2011.
non-patent document 8: Rothe, C. et al. J. Mol. Biol. 376: 1182-1200, 2008.

SUMMARY OF THE INVENTION

Problems to be Solved by the Invention

An object of the present invention is to provide an anti-human CD69 antibody applicable to the prophylaxis or treatment of allergic diseases and inflammatory diseases.

Means of Solving the Problems

To solve the above-mentioned problem, the present inventors first produced an anti-CD69 antibody that binds to both human CD69 and mouse CD69. In addition, they intensively studied a method of evaluating a pharmacological effect of anti-human CD69 antibody in vivo. As a result, they have succeeded in reproducing an allergic reaction in mouse, which is mediated by Th2 cells that express human OD69, by forcibly expressing human CD69 in Th2 cells of CD69 deficient mouse immunized with a particular antigen, and returning the Th2 cells into the body of the mouse. They have produced a plurality of anti-human CD69 antibodies by HuCAL, and evaluated the effect on the allergic reaction by using the aforementioned mouse. As a result, they have found an anti-human CD69 antibody having superior allergy suppressing effect and inflammation—suppressing effect. Furthermore, they have improved the affinity for human CD69 by modifying the light chain CDR3 of the obtained antibody, and succeeded in potentiating the allergy suppressing effect and inflammation-suppressing effect, while maintaining the cross-reactivity with mouse CD69. Based on the above-mentioned findings, they have completed the present invention.

Accordingly, the present invention relates to the following.

[1] An antibody that specifically binds to human CD69, has an activity to suppress allergic inflammation, and has cross reactivity with mouse CD69.

[2] The antibody of [1] that binds to human. CD69 at an epitope comprising the amino acid sequence shown by SEQ ID NO: 33.

[3] The antibody of [1], comprising a light chain variable region and a heavy chain variable region, wherein
(1) the light chain variable region comprises CDR1 comprising the amino acid sequence shown in SEQ ID NO: 7, CDR2 comprising so the amino acid sequence shown in SEQ ID NO: 8 and CDR3 comprising the amino acid sequence shown in. SEQ ID NO: 9, 19 or 20, and
the heavy chain variable region comprises CDR1 comprising the amino acid sequence shown in SEQ ID NO: 10, CDR2 comprising the amino acid sequence shown in SEQ ID NO: 11 and CDR3 comprising the amino acid sequence shown in SEQ ID NO: 12, or
(2) the light chain variable region comprises CDR1 comprising the amino acid sequence shown in SEQ ID NO: 7, CDR2 comprising the amino acid sequence shown in SEQ ID NO: 8 and CDR3 comprising the amino acid sequence shown in SEQ ID NO: 9, 19 or 20, and
the heavy chain variable region comprises CDR1 comprising the amino acid sequence shown in SEQ ID NO: 10, CDR2 comprising the amino acid sequence shown in SEQ ID NO: 11 and CDR3 comprising the amino acid sequence shown in SEQ ID NO: 12,
except that 1 to 3 amino acids are substituted, deleted, inserted, and/or added in at least one amino acid sequence selected from the group consisting of the amino acid sequences shown in SEQ ID NOs: 7-9, 19 and 20, and/or
1 to 3 amino acids are substituted, deleted, inserted, and/or added in at least one amino acid sequence selected from the group consisting of the amino acid sequences shown in SEQ ID NOs: 10-12.

[4] The antibody of [3], wherein
(1') the light chain variable region comprises the amino acid sequence shown in SEQ ID NO: 23, 27 or 28, and the heavy chain variable region comprises the amino acid sequence shown by SEQ ID NO: 24.

[5] An antibody that specifically binds to human CD69, has an activity to suppress allergic inflammation, and binds to human CD69 at an epitope comprising the amino acid sequence shown by SEQ ID NO: 59 or 78.

[6] An antibody that specifically binds to human CD69, has an activity to suppress allergic inflammation, and comprises a light chain variable region and a heavy chain variable region, wherein
(3) the sight chain variable region comprises CDR1 comprising the amino acid sequence shown in SEQ ID NO: 1, CDR2 comprising the amino acid sequence shown in SEQ ID NO: 2 and CDR3 comprising the amino acid sequence shown in SEQ ID NO: 3, and the heavy chain variable region comprises CDR1 comprising the amino acid sequence shown in SEQ ID NO: 4, CDR2 comprising the amino acid sequence shown in SEQ ID NO: 5 and CDR3 comprising the amino acid sequence shown in SEQ ID NO: 6,
(4) the light chain variable region comprises CDR1 comprising the amino acid sequence shown in SEQ ID NO: 13, CDR2 comprising the amino acid sequence shown in SEQ ID NO: 14 and CDR3 comprising the amino acid sequence shown in SEQ ID NO: 15, and the heavy chain variable region comprises CDR1 comprising the amino acid sequence shown in SEQ ID NO: 16, CDR2 comprising the amino acid sequence shown in SEQ ID NO: 17 and CDR3 comprising the amino acid sequence shown in SEQ ID NO: 18;
(5) the light chain variable region comprises CDR1 comprising the amino acid sequence shown in SEQ ID NO: 1, CDR2 comprising the amino acid sequence shown in SEQ ID NO: 2 and CDR3 comprising the amino acid sequence shown in SEQ ID NO: 3, and the heavy chain variable region comprises CDR1 comprising the amino acid sequence shown in SEQ ID NO: 4, CDR2 comprising the amino acid sequence shown in SEQ ID NO: 5 and CDR3 comprising the amino acid sequence shown in SEQ ID NO: 6,
except that 1 to 3 amino acids are substituted, deleted, inserted, and/or added in at least one amino acid sequence selected from the group consisting of the amino acid sequences shown in SEQ ID NOs: 1 to 3, and/or
1 to 3 amino acids are substituted, deleted, inserted, and/or added in at least one amino acid sequence selected from the group consisting of the amino acid sequences shown in SEQ ID NOs: 4 to 6; or
(6) the light chain variable region comprises CDR1 comprising the amino acid sequence shown in SEQ ID NO: 13, CDR2 comprising the amino acid sequence shown in SEQ ID NO: 14 and CDR3 comprising the amino acid sequence shown in SEQ ID NO: 15, and the heavy chain variable region comprises CDR1 comprising the amino acid sequence shown in SEQ ID NO: 16, CDR2 comprising the amino acid sequence shown in SEQ ID NO: 17 and CDR3 comprising the amino acid sequence shown in SEQ ID NO: 18,
except that 1 to 3 amino acids are substituted, deleted, inserted, and/or added in at least one amino acid sequence selected from the group consisting of the amino acid sequences shown in SEQ ID NOs: 13 to 15, and/or
1 to 3 amino acids are substituted, deleted, inserted, and/or added in at least one amino acid sequence selected from the group consisting of the amino acid sequences shown in SEQ ID NOs: 16 to 18.

[7] The antibody of [6], wherein
(3') the light chain variable region comprises the amino acid sequence shown in SEQ ID NO: 21, and the heavy chain variable region comprises the amino acid sequence shown by SEQ ID NO: 22; or
(4') the light chain variable region comprises the amino acid sequence shown in SEQ ID NO: 25, and the heavy chain variable region comprises the amino acid sequence shown by SEQ ID NO: 26.

[8] The antibody of any of [1]-[7], which has a $K_D$ value of not more than $5 \times 10^{-8}$ N relating to binding affinity to human CD69.

[9] The antibody of any of [1]-[8], which is a human antibody.

[10] A pharmaceutical composition comprising the antibody of any of [1]-[9].

[11] A prophylactic or therapeutic agent for an allergic disease or inflammatory disease, comprising the antibody of any of [1]-[9].

[12] A polynucleotide encoding the antibody of any of [1]-[9].

[13] A vector comprising the polynucleotide of [12].

[14] A transformant comprising the vector of [13].

[15] A non-human mammal comprising transferred Th2 cells of CD69 deficient non-human mammal immunized with a particular antigen, wherein the Th2 cells express human CD69.

[16] The non-human mammal of [15], wherein the non-human mammal is a mouse.

[17] The antibody of any of [1]-[9], for use in the prophylaxis or treatment of an allergic disease or inflammatory disease.

[18] A method for the prophylaxis or treatment of an allergic disease or inflammatory disease in a mammal, comprising administering an effective amount of the antibody of any of [1]-[9] to said mammal.

[19] Use of the antibody of any of [1]-[9] for producing an agent for the prophylaxis or treatment of an allergic disease or inflammatory disease.

Effect of the Invention

According to the present invention, an anti-human CD69 antibody applicable to the prophylaxis or treatment of allergic diseases and inflammatory diseases is provided. According to the present invention, moreover, an animal model permitting in vivo evaluation of a pharmacological effect of an anti-human CD69 antibody can be provided.

BRIEF DESCRIPTION OF THE DRAWINGS

FIG. 6 shows alignment of the amino acid sequences of mouse CD69 (upper sequence) and human CD69 (lower sequence).

DESCRIPTION OF EMBODIMENTS

Figure 1:
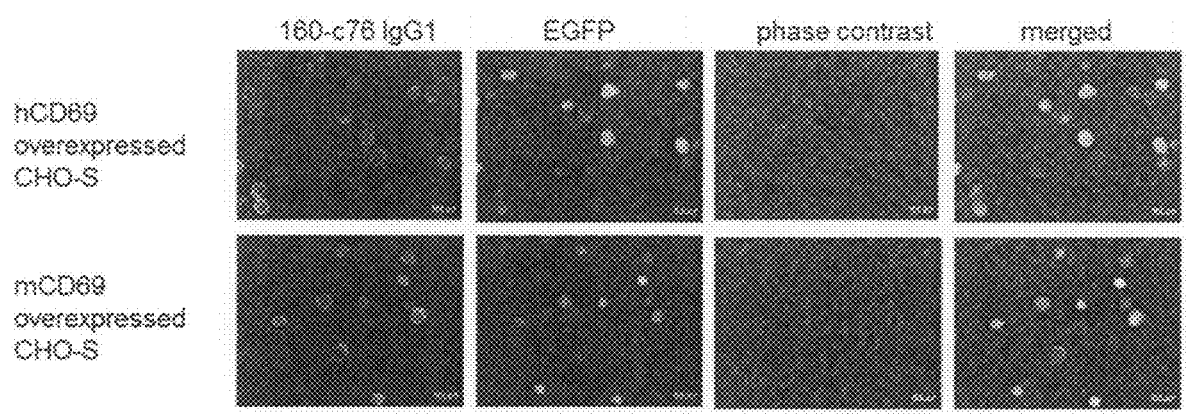
FIG. 1 shows evaluation of binding to human CD69 and mouse CD69 by cell staining.

The present invention provides an antibody having a specific binding activity to human CD69, and an activity to suppress allergic inflammation.

CD69 is a known TYPE II membrane protein, and the amino acid sequence thereof and the cDNA sequence thereof are also known. A representative amino acid sequence of human CD69 is shown in SEQ ID NO: 30, a representative cDNA sequence of human CD69 is shown in SEQ ID NO: 29, a representative amino acid sequence of mouse CD69 is shown in SEQ ID NO: 32, and a representative cDNA sequence of mouse CD69 is shown in SEQ ID NO: 31.

The antibody of the present invention has a specific binding activity to an extracellular domain of human CD69. The extracellular domain of human CD69 corresponds to the region of 62-199 in the amino acid sequence shown by SEC ID NO: 30, and the extracellular domain of mouse CD69 corresponds to the region of 62-199 in the amino acid sequence shown by SEQ ID NO: 32.

The "human CD69" means that the amino acid sequence or nucleic acid sequence of CD69 has an amino acid sequence or nucleic acid sequence which is the same as or substantially the same as the amino acid sequence or nucleotide sequence of CD69 naturally expressed in human. The "substantially the same" means that the amino acid sequence or nucleic acid sequence of interest has 70% or more (preferably 80% or more, more preferably 90% or more, further preferably 95% or more, most preferably 99% or more) identity with the amino acid sequence or nucleic acid sequence of a particular CD69 naturally expressed in human, and has the function of the particular human CD69. Biological species other than human, proteins other than CD69, gene and fragments thereof are also interpreted in the same manner.

The "specific binding" of an antibody to antigen X means that the $K_D$ value of the binding affinity of an antibody to antigen X in an antigen-antibody reaction is not more than $1 \times 10^{-7}$ M.

In the present specification, the $K_D$ value relating to the binding affinity of the antibody of the present invention to human CD69 is calculated according to the principle described in Immunoassays (OXFORD UNIVERSITY PRESS, 2000) using a scatchard plot method. An antibody is incubated with various concentrations of antigen (extracellular domain of human CD69) at room temperature for 2 hr until equilibrium, and the amount of free antibody present in the incubation solutions is measured by the ELISA method. The binding constant and dissociation constant ($K_D$ value) are determined based on the changes in the amount of free antibody in each equilibrated sample. The antibody concentration during equilibration reaction is to be 0.015 μg/ml, and an ELISA plate for the measurement of the amount of free antibody is to be immobilized with the antigen at 1 μg/ml.

In a preferable embodiment, the $K_D$ value relating to the binding affinity of the antibody of the present invention to human CD69 is not more than $5 \times 10^{-8}$ M.

The antibody of the present invention has an activity to so suppress allergic inflammations. Allergic inflammation refers to inflammations characterized by selective accumulation of mononuclear cells in the target tissue, which occurs in association with allergic reactions. Mononuclear cell encompasses Th2 cells, eosinophils, basophils and mast cells. Whether or not an antibody has an activity to suppress allergic inflammations can be confirmed by evaluating whether or not it suppresses an allergic reaction (e.g., leukocyte infiltration) induced by exposing the below-mentioned non-human mammal of the present invention to an antigen.

In the present specification, the "antibody" is used as one encompassing a full-length antibody and any antigen-binding fragment (i.e., "antigen-binding portion") thereof or a single chain thereof. The "antibody" refers to a glycoprotein containing at least two heavy chains (H) and two light chains (L), which are linked by a disulfide bond, or an antigen-binding portion thereof. Each heavy chain is constituted by a heavy chain variable region (to be abbreviated as $V_H$ herein) and a heavy chain constant region. The heavy chain constant region is constituted by 3 domains of $C_H1$, $C_H2$ and $C_H3$. Each light chain is constituted by a light chain variable region (to be abbreviated as $V_L$ herein) and a light chain constant region. The light chain constant region is constituted by a single domain $C_L$. $V_H$ and $V_L$ regions are further subdivided into regions with higher variability called complementarity determining regions (CDRs), which contain more highly conservative regions called framework regions (ERs) scattered therein. Each $V^H$ and $V_L$ is constituted by 3 CDRs and 4 FRs, which are aligned in the following order, i.e., FR1, CDR1, FR2, CDR2, FR3, CDR3, FR4 from the amino terminus to the carboxy terminus. The variable regions of said heavy chain and light chain contain binding domains that interact with an antigen. The constant region of an antibody can mediate the binding of immunoglobulin to host tissues or factors, including various cells (e.g., effector cells) of the immune system and the first component. (C1q) of the conventional complement system.

In the present specification, the "antigen-binding portion" of an antibody is used to refer to one or more fragments of an antibody retaining an ability to specifically bind to an antigen (e.g., human CD69). It has been clarified that the antigen binding function of an antibody is performed by a fragment of a full-length antibody. Examples of the binding fragment included in the term "antigen binding portion." of an antibody include (i) Fab fragment, a monovalent fragment constituted by $V_L$, $V_H$, $C_L$ and $C_{H1}$ domains, (ii) $F(ab')_2$ fragment, a divalent fragment containing two Fab fragments linked by disulfide bond in the hinge region, (iii) Fab' fragment, an inherent Fab having a hinge region portion (see FUNDAMENTAL IMMUNOLOGY, Paul ed., 3. sup, rd ed. 1993), (iv) Fd fragment constituted by $V_H$ and $C_{H1}$ domains, (v) Fv fragment constituted by $V_L$ and $V_H$ domains in a single arm of an antibody, (vi) dAb fragment constituted by $V_H$ domain (Ward et al., (1989) Nature 341:544-546), (vii) isolated complementarity determining region (CDR) and (viii) nanobody which is a heavy chain variable region containing single variable domain and two constant regions. While $V_L$ and $V_H$, which are the two domains of Fv fragment, are encoded by different genes, they can be linked by a synthetic linker to produce a single protein chain from them by recombinant techniques, wherein, in this chain, $V_L$ and $V_H$ regions pair with each other to form a monovalent molecule (known as a single chain Fv (scFv); see, for example, Bird et. al. (1988) Science 212: 423-426; and Huston et al., (1988) Proc. Natl. Acad. Sci. USA 85: 5879-5883). Such single chain antibody is also encompassed in the "antigen-binding portion" of an antibody. Such antibody fragments are obtained by those of ordinary skill in the art by known conventional techniques, and screened for usefulness in the same manner as with unmodified antibody.

The antibody of the present invention is preferably a monoclonal antibody. The "monoclonal antibody" refers to a preparation of an antibody molecule of a single molecule composition. The monoclonal antibody composition shows single binding-specificity and affinity for a particular portion of an antigen called epitope.

The antibody of the present invention is preferably a human antibody. The "human antibody" refers to an antibody having variable regions derived from a human germline immunoglobulin sequence in both the framework and CDR regions. Furthermore, when an antibody contains a constant region, the constant region also derives from a human germline immunoglobulin sequence. In the present specification, the "human antibody" also encompasses even an embodiment including an amino acid residue not encoded by a human germline immunoglobulin sequence (e.g., mutation introduced by random or site-directed mutagenesis in vitro or somatic mutation in vivo). In the present specification, however, the term of the "human antibody" is not intended to include an antibody wherein a CDR sequence derived from the germline of an animal species other than human, such as mouse, is fused on the human framework sequence.

In the present specification, the human antibody encompasses a "reconstituted human antibody". The reconstituted human antibody refers to a modified antibody wherein at least one CDR contained in the first human donor antibody is used in the second human acceptor antibody, instead of CDR of the second human acceptor antibody. Preferably, all 6 CDRs are substituted. More preferably, the whole antigen binding region (e.g., Fv, Fab or F(ab')2) of the first human donor antibody is used instead of the corresponding region in so the second human acceptor antibody. More preferably, the Fab region of the first human donor antibody is operably linked to an appropriate constant region of the second human acceptor antibody to form a full-length antibody.

The reconstituted human antibody can be produced by conventional gene recombinant techniques disclosed in, for example, EP125023, WO96/02576, non-patent document 8 and the like. To be specific, for example, a DNA sequence designed to link a desired CDR in a donor human antibody and a desired framework region (FR) in an acceptor human antibody is synthesized by PCR method using, as primers, several oligonucleotides produced to have a region overlapping with the terminus regions of both CDR and FR (see the method described in WO98/13388). The obtained DNA is linked to a DNA encoding a human antibody constant region or a human antibody constant region mutant, which is incorporated into a expression vector and the vector is introduced into a host to allow for production, whereby a reconstituted human antibody can be obtained (see EP125023, WO96/02576).

In the present specification, moreover, the human antibody encompasses an "artificial human antibody". The artificial human antibody can be produced by conventional gene recombinant techniques disclosed in, for example, non-patent document 8 and the like.

The antibody of the present invention also includes a fusion protein wherein the aforementioned antibody and other peptide or protein are fused. The production method of a fusion protein includes linking a polynucleotide encoding the antibody of the present invention and a polynucleotide encoding other peptide or polypeptide to match the frame, introducing same into an expression vector, and allowing expression thereof in a host, and techniques known to those of ordinary skill in the art can be used. As other peptide to be fused with the antibody of the present invention, known peptides such as FLAG (Hopp, T. P. et al., BioTechnology (1988) 6, 1204-1210), 6×His consisting of six His (histidine) residues, 10×His, human c-myc fragment, VSV-GP fragment, p18HIV fragment, TV-tag, HSV-tag, tag, SV40T antigen fragment, ink tag, α-tubulin fragment, B-tag, Protein C fragment and the like can be used. Examples of other polypeptide to be fused with the antibody of the present invention include GST (glutathione-S-transferase), HA (influenza hemaggiutinin), immunoglobulin constant region, β-galactosidase, MBP (maltose binding protein.) and the like. A commercially available polynucleotide encoding such peptide or polypeptide is fused with a polynucleotide encoding the antibody of the present invention, and a fusion polynucleotide prepared thereby is expressed, whereby a fusion polypeptide can be prepared.

The antibody of the present invention may be a conjugate antibody bound with various molecules, for example, polymer substances such as polyethylene glycol (PEG), hyaluronic acid and the like, radioactive substance, fluorescent substance, luminescence substance, enzyme, toxin and the like. Such conjugate antibody can be obtained by chemically modifying the obtained antibody. The modification method of antibody has already been established in this field (e.g., U.S. Pat. Nos. 5,057,313, 5,156,840).

The antibody of the present invention is preferably isolated or purified. Being "isolated or purified" means that an operation to remove components other than the component of interest has been applied to the state of natural presence.

The purity of the isolated or purified antibody of the present invention (ratio of the weight of the antibody of the present so invention to the total protein weight) is generally 50% or more, preferably 70% or more, more preferably 90% or more, most preferably 95% or more (e.g., substantially 100%).

In one embodiment, the antibody of the present invention has cross-reactivity with mouse CD69 (preferably extracellular domain of mouse CD69). The "cross-reactivity" means that an antibody that specifically binds to human CD69 also binds to mouse CD69 (preferably extracellular domain of mouse CD69) by antigen-antibody reaction. The antibody of the present invention having cross-reactivity with mouse CD69 is superior in that it can evaluate efficacy even in mouse not expressing human CD69.

In a preferable embodiment, the antibody of the present invention having cross-reactivity with mouse CD69 binds to human CD69 at an epitope containing the amino acid sequence shown by SEQ ID NO: 33 (YNCPG). The epitope containing the amino acid sequence shown in SEQ ID NO: 33 includes, for example, an epitope consisting of a continuous partial sequence of the amino acid sequence shown in SEQ ID NO: 30, which contains the amino acid sequence shown in SEQ ID NO: 33, and has an amino acid length of 12 or less. As the epitope containing the amino acid sequence shown by SEQ ID NO: 33, specifically, an epitope consisting of the amino acid sequence shown by SEQ ID NO: 35, and an epitope consisting of the amino acid sequence shown by SEQ ID NO: 36 can be mentioned.

As the antibody of the present invention having cross-reactivity with mouse CD69, the antibodies described in the following (1) and (2) can be mentioned:
(1) an antibody comprising a light chain variable region and a heavy chain variable region,
wherein the light chain variable region comprises CDR1 comprising the amino acid sequence shown in SEQ ID NO: 7, CDR2 comprising the amino acid sequence shown in SEQ ID NO: 8 and CDR3 comprising the amino acid sequence shown in SEQ ID NO: 9, 19 or 20, and
the heavy chain variable region comprises CDR1 comprising the amino acid sequence shown in SEQ ID NO: 10, CDR2 comprising the amino acid sequence shown in SEQ ID NO: 11 and CDR3 comprising the amino acid sequence shown in SEQ ID NO: 12; and
(2) an antibody comprising a light chain variable region and a heavy chain variable region,
wherein the light chain variable region comprises CDR1 comprising the amino acid sequence shown in SEQ ID NO: 7, CDR2 comprising the amino acid sequence shown in SEQ ID NO: 8 and CDR3 comprising the amino acid sequence shown in SEQ ID NO: 9, 19 or 20, and
the heavy chain variable region comprises CDR1 comprising the amino acid sequence shown in SEQ ID NO: 10, CDR2 comprising the amino acid sequence shown in SEQ ID NO: 11 and CDR3 comprising the amino acid sequence shown in SEQ ID NO: 12
except that 1 to 3 amino acids are substituted, deleted, inserted, and/or added in at least one amino acid sequence selected from the group consisting of the amino acid sequences shown in SEQ ID NOs: 7-9, 19 and 20, and/or 1 to 3 amino acids are substituted, deleted, inserted, and/or added in at least one amino acid sequence selected from the group consisting of the amino acid sequences shown in SEQ ID NOs: 10-12.

The antibody described in the above-mentioned (1) or (2) can bind to human CD69 at an epitope comprising the amino acid sequence shown by SEQ ID NO: 33 (preferably, an epitope consisting of a continuous partial sequence of the amino acid sequence shown in SEQ ID NO: 30, which contains the amino acid sequence shown in. SEQ ID NO: 33, and has an amino acid length of 12 or less; more preferably, epitope consisting of the amino so acid sequence shown by SEQ ID NO: 35 or SEQ ID NO: 36).

In one embodiment, the antibody of the present invention binds to human CD69 at an epitope consisting of the amino acid sequence shown by SEQ ID NO: 59.

In one embodiment, the antibody of the present invention binds to human CD69 at an epitope containing the amino acid sequence shown by SEQ ID NO: 78 (YAGREE). The epitope containing the amino acid sequence shown in SEQ ID NO: 78 includes, for example, an epitope consisting of a continuous partial sequence of the amino acid sequence shown in SEQ ID NO: 30, which contains the amino acid sequence shown in SEQ ID NO: 78, and has an amino acid length of 12 or less. As the epitope containing the amino acid sequence shown by SEQ ID NO: 78, specifically, an epitope consisting of the amino acid sequence shown by SEQ ID NO: 57, an epitope consisting of the amino acid sequence shown by SEQ ID NO: 58 and an epitope consisting of the amino acid sequence shown by SEQ ID NO: 59 can be mentioned.

As other antibody of the present invention, the antibodies described in the following (3)-(6) can be mentioned:
(3) an antibody comprising a light chain variable region and a heavy chain variable region,
wherein the light chain variable region comprises CDR1 comprising the amino acid sequence shown in SEQ ID NO: 1, CDR2 comprising the amino acid sequence shown in SEQ ID NO: 2 and CDR3 comprising the amino acid sequence shown in SEQ ID NO: 3, and
the heavy chain variable region comprises CDR1 comprising the amino acid sequence shown in SEQ ID NO: 4, CDR2 comprising the amino acid sequence shown in SEQ ID NO: 5 and CDR3 comprising the amino acid sequence shown in SEQ ID NO: 6;
(4) an antibody comprising a light chain variable region and a heavy chain variable region,
wherein the light chain variable region comprises CDR1 comprising the amino acid sequence shown in SEQ ID NO: 13, CDR2 comprising the amino acid sequence shown in SEQ ID NO: 14 and CDR3 comprising the amino acid sequence shown in SEQ ID NO: 15, and
the heavy chain variable region comprises CDR1 comprising the amino acid sequence shown in SEQ ID NO: 16, CDR2 comprising the amino acid sequence shown in SEQ ID NO: 17 and CDR3 comprising the amino acid sequence shown in SEQ ID NO: 18;
(5) an antibody comprising a light chain variable region and a heavy chain variable region,
wherein the light chain variable region comprises CDR1 comprising the amino acid sequence shown in SEQ ID NO: 1, CDR2 comprising the amino acid sequence shown in SEQ ID NO: 2 and CDR3 comprising the amino acid sequence shown in SEQ ID NO: 3, and
the heavy chain variable region comprises CDR1 comprising the amino acid sequence shown in SEQ ID NO: 4, CDR2 comprising the amino acid sequence shown in SEQ ID NO: 5 and CDR3 comprising the amino acid sequence shown in SEQ ID NO: 6,
except that 1 to 3 amino acids are substituted, deleted, inserted, and/or added in at least one amino acid sequence selected from the group consisting of the amino acid sequences shown in SEQ ID NOs: 1 to 3, and/or 1 to 3 amino acids are substituted, deleted, inserted, and/or added in at least one amino acid sequence selected from the group consisting of the amino acid sequences shown in SEQ ID NOs: 4 to 6; and (6) an antibody comprising a light chain variable region and a heavy chain variable region, wherein the light chain variable region comprises CDR1 comprising the amino acid sequence shown in SEQ ID NO: 13, CDR2 comprising the amino acid sequence shown in SEQ ID NO: 14 and CDR3 comprising the amino acid sequence shown in SEQ ID NO: 15, and the heavy chain variable region comprises CDR1 comprising the amino acid sequence shown in SEQ ID NO: 16, CDR2 comprising the amino acid sequence shown in SEQ ID NO: 17 and CDR3 comprising the amino acid sequence shown in SEQ ID NO: 18, except that 1 to 3 amino acids are substituted, deleted, inserted, and/or added in at least one amino acid sequence selected from the group consisting the amino acid sequences shown in SEQ ID NOs: 13 to 15, and/or 1 to 3 amino acids are substituted, deleted, inserted, and/or added in at least one amino acid sequence selected from the group consisting of the amino acid sequences shown in SEQ ID NOs: 16 to 18.

The antibody described in the above-mentioned (3) or (5) can bind to human CD69 at an epitope consisting of the amino acid sequence shown by SEQ ID NO: 59.

The antibody described in the above-mentioned (4) or (6) can bind to human CD69 at an epitope consisting of the amino acid sequence shown by SEQ ID NO: 78 (preferably, an epitope consisting of a continuous partial sequence of the amino acid sequence shown in SEQ ID NO: 30, which contains the amino acid sequence shown in SEQ ID NO: 78, and has an amino acid length of 12 or less; more preferably, an epitope consisting of the amino acid sequence shown by SEQ ID NO: 57, SEQ ID NO: 58 or SEQ ID NO: 59).

The $K_D$ value of the antibody described in (1) relating to the binding affinity to human CD69 is preferably not more than $3 \times 10^{-8}$ M. When CDR3 in the light chain variable region has the amino acid sequence shown by SEQ ID NO: 19, the $K_D$ value of the antibody relating to the binding affinity to human CD69 is preferably not more than $1 \times 10^{-8}$ M, more preferably not more so than $5 \times 10^{-9}$ M, further preferably not more than $2 \times 10^{-9}$ M. When CDR3 in the light chain variable region has the amino acid sequence shown by SEQ ID NO: 20, the $K_D$ value of the antibody relating to the binding affinity to human CD69 is preferably not more than $1 \times 10^{-8}$ M, more preferably not more than $5 \times 10^{-9}$ M, further preferably not more than $3 \times 10^{-9}$ M.

The $K_D$ value of the antibody described in (2) relating to the binding affinity to human CD69 is preferably not more than $3 \times 10^{-8}$ M.

When the antibody described in (2) is an antibody comprising a light chain variable region and a heavy chain variable region, wherein the light chain variable region comprises CDR1 comprising the amino acid sequence shown in SEQ ID NO: 7, CDR2 comprising the amino acid sequence shown in SEQ ID NQ: 8 and CDR3 comprising the amino acid sequence shown in SEQ ID NO: 19, and the heavy chain variable region comprises CDR1 comprising the amino acid sequence shown in SEQ ID NO: 10, CDR2 comprising the amino acid sequence shown in SEQ ID NO: 11 and CDR3 comprising the amino acid sequence shown in SEQ ID NO: 12, except that 1 to 3 amino acids are substituted, deleted, inserted, and/or added in at least one amino acid sequence selected from the group consisting of the amino acid sequences shown in SEQ ID NOs: 7, 8 and 19, and/or 1 to 3 amino acids are substituted, deleted, inserted, and/or added in at least one amino acid sequence selected from the group consisting of SEQ ID NOs: 10 to 12, the $K_D$ value of the antibody relating to the binding affinity to human CD69 is preferably not more than $1 \times 10^{-8}$ M, more preferably not more than $5 \times 10^{-9}$ M, further preferably not more than $2 \times 10^{-9}$ M.

When the antibody described in (2) is an antibody comprising a light chain variable region and a heavy chain variable region, wherein the light chain variable region comprises CDR1 comprising the amino acid sequence shown in SEQ ID NO: 7, CDR2 comprising the amino acid sequence shown in SEQ ID NO: 8 and CDR3 comprising the amino acid sequence shown in SEQ ID NO: 20, and the heavy chain variable region comprises CDR1 comprising the amino acid sequence shown in SEQ ID NQ: 10, CDR2 comprising the amino acid sequence shown in SEQ ID NO: 11 and CDR3 comprising the amino acid sequence shown in SEQ ID NO: 12, except that 1 to 3 amino acids are substituted, deleted, inserted, and/or added in at least one amino acid sequence selected from the group consisting of the amino acid sequences shown in SEQ ID NOs: 7, 8 and 20, and/or 1 to 3 amino acids are substituted, deleted, inserted, and/or added in at least one amino acid sequence selected from the group consisting of the amino acid sequences SEQ ID NOs: 10-12, the $K_D$ value relating to the binding affinity of the antibody to human CD69 is preferably not more than $1 \times 10^{-8}$ M, more preferably not more than $5 \times 10^{-9}$ M, further preferably not more than $3 \times 10^{-9}$ M.

The $K_D$ value of the antibody described in (3) or (5) relating to the binding affinity to human CD69 is preferably not more than $5 \times 10^{-8}$ M.

The $K_D$ value of the antibody described in (4) or (6) relating to the binding affinity to human CD69 is preferably not more than $8 \times 10^{-9}$ M.

In the embodiments of (2), (5) and (6), the number of amino acids to be substituted, deleted, inserted and/or added is not particularly limited as long as the antibody specifically binds to human CD69, and has an activity to suppress allergic inflammation. It is preferably within 2 amino acids, more preferably one amino acid, per one CDR sequence. While the number of CDR sequences in which amino acid is substituted, deleted, inserted and/or added is not particularly limited as long as the antibody specifically binds to human CD69, and has an activity to suppress allergic inflammation. It is preferably within 2, more preferably one, per one light chain variable region, and preferably within 2, more preferably 1, per one heavy chain variable region. The substitution, deletion, insertion and/or addition of amino acid may be performed in both the light chain variable region and the heavy chain variable region, or either one of them.

In the embodiments of (2), (5) and (6), 1-3 (preferably 1 or 2, more preferably 1) amino acids are preferably substituted, deleted, inserted, and/or added only in the amino acid sequence of CDR3 in the light chain variable region.

In the embodiment of (2), when 1 to 3 amino acids are substituted, deleted, inserted and/or added in the amino acid sequence of CDR3 in the light chain variable region, it is preferable to maintain serine of the 2nd and tyrosine of the 3rd of the amino acid sequence of the CDR3. The first amino acid of the amino acid sequence of the CDR3 is mutually substitutable between glutamine and glycine. The 4th amino acid of the amino acid sequence of the CDR3 is mutually substitutable between aspartic acid and threonine. The 5th amino acid of the amino acid sequence of the CDR3 is mutually substitutable between serine and threonine.

Examples of the method for substituting one or plural amino acid residues with other desired amino acid include site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Using these methods, desired amino acid in an antibody can be substituted by other amino acid of interest. Also, using the library technique such as framework shuffling (Mol Immunol. 2007 April; 44(11): 3049-60) and CDR repair (US2006/0122377) and the like, an amino acid in a framework or CDR can also be substituted by other appropriate amino acid.

In the antibody of the present invention, as a framework region (FR) of the antibody to be linked to a CDR, a framework which enables the CDR to form a good antigen binding site is selected. While FR to be used for the antibody of the present invention is not particularly limited and any FR can be used, FR of a human antibody is preferably used. As the FR of a human antibody, one having a natural sequence may be used, or one or plural amino acids in the framework region having a natural sequence may be substituted, deleted, added and/or inserted and the like as necessary, so that CDR will form an appropriate antigen binding site. For example, a mutant FR sequence having desired properties can be selected by measuring and evaluating the binding activity of an antibody having FR with substituted amino acid to an antigen (Sato, K. et al., Cancer Res. (1993) 53, 851-856).

In the antibodies of (1) and (2), FR of Vl3 (Kabat database) of human antibody is preferably used for the light chain, and FR of VH3 (Kabat database) of human antibody is preferably used for the heavy chain.

In the antibodies of (3) and (5), FR of Vl3 (Kabat database) of human antibody is preferably used for the light chain, and FR of VH1B (Kabat database) of human antibody is preferably used for the heavy chain.

In the antibodies of (4) and (6), FR of Vk3 (Kabat database) of human antibody is preferably used for the light chain, and FR of VH3 (Rabat database) of human antibody is preferably used for the heavy chain.

The constant region used for the antibody of the present invention is not particularly limited, and any constant region may be used. Preferable examples of the constant region used for the antibody of the present invention include constant regions of human antibody (constant regions derived from IgG1, IgG2, IgG3, IgG4, IgA, IgM and the like). For example, Cγ1, Cγ2, Cγ3, Cγ4, Cμ, Cδ, Cα1, Cα2, Cε can be used in H chain, and Cκ, Cλ can be used in L chain.

In the antibodies of (1) and (2), the constant region of Cλ of human antibody is preferably used for the light chain, and the constant region of Cγ4 of human antibody is preferably used for the heavy chain.

In the antibodies of (3) and (5), the constant region of Cκ of human antibody is preferably used for the light chain, and the constant region of Cγ4 of human antibody is preferably used for the heavy chain.

In the antibodies of (4) and (6), the constant region of Cκ of human antibody is preferably used for the light chain, and the constant region of Cγ4 of human antibody is preferably used for the heavy chain.

Preferable antibody of the present invention includes the following:

(1') An antibody comprising a light chain variable region and a heavy chain variable region, wherein the light chain variable so region comprises the amino acid sequence shown in SEQ ID NO: 23, 27 or 28 and the heavy chain variable region comprises the amino acid sequence shown in SEQ ID NO: 24;

(3') an antibody comprising a light chain variable region and a heavy chain variable region, wherein the light chain variable region comprises the amino acid sequence shown in SEQ ID NO: 21 and the heavy chain variable region comprises the amino acid sequence shown in SEQ ID NO: 22; and (4') an antibody comprising a light chain variable region and a heavy chain variable region, wherein the light chain variable region comprises the amino acid sequence shown in SEQ ID NO: 25 and the heavy chain variable region comprises the amino acid sequence shown in SEQ ID NO: 26.

The antibody of the above-mentioned (1') corresponds to a preferable embodiment of the antibody of the above-mentioned (1), the antibody of the above-mentioned (3') corresponds to a preferable embodiment of the antibody of the above-mentioned (3), and the antibody of the above-mentioned (4') corresponds to a preferable embodiment of the antibody of the above-mentioned (4), respectively.

The antibody described in the above-mentioned (1') can bind to human CD69 at an epitope comprising the amino acid sequence shown by SEQ ID NO: 33 (preferably, an epitope consisting of a continuous partial sequence of the amino acid sequence shown in SEQ ID NO: 30, which contains the amino acid sequence shown in SEQ ID NO: 33, and has an amino acid length of 12 or less; more preferably, epitope consisting of the amino acid sequence shown by SEQ ID NO: 35 or SEQ ID NO: 36).

The antibody described in the above-mentioned (3') can bind to human CD69 at an epitope consisting of the amino acid sequence shown by SEQ ID NO: 59.

The antibody described in the above-mentioned (4') can bind to human CD69 at an epitope comprising the amino acid sequence shown by SEQ ID NO: 78 (preferably, an epitope consisting of a continuous partial sequence of the amino acid sequence shown in SEQ ID NO: 30, which contains the amino acid sequence shown in SEQ ID NO: 78, and has an amino acid length of 12 or less; more preferably, an epitope consisting of the amino acid sequence shown by SEQ ID NO: 57, SEQ ID NO: 58 or SEQ ID NO: 59).

The present invention provides a polynucleotide containing a nucleotide sequence encoding the above-mentioned antibody of the present invention. The polynucleotide may be a DNA or RNA, or a DNA/RNA chimera. The polynucleotide may be double stranded or single stranded. When the polynucleotide is double stranded, it may be a double stranded DNA, a double stranded RNA or a DNA:RNA hybrid.

The polynucleotide of the present invention encompasses a polynucleotide containing a nucleotide sequence encoding both the heavy chain variable region and the light chain variable region of the antibody of the present invention, and a combination of a polynucleotide containing a nucleotide sequence encoding the heavy chain variable region of the antibody of the present invention and a polynucleotide containing a nucleotide sequence encoding the light chain variable region of the antibody of the present invention.

The polynucleotide of the present invention can be easily produced based on the information of the amino acid sequence of the antibody of the present invention, known sequence information and sequence information described in the Sequence Listing in the present specification, and by utilizing known gene recombination techniques. For example, suitable primers are designed based on the sequence information, a DNA encoding so the elements constituting the antibody of the present invention is amplified by the POE reaction, DNA fragments are ligated by appropriate enzymes such as ligase and the like, whereby the polynucleotide of the present invention can be produced. Alternatively, a polynucleotide encoding each element may be synthesized by a polynucleotide synthesizer, based on the information of the amino acid sequence of the antibody of the present invention.

The obtained polynucleotide encoding the antibody of the present invention may be, depending on the object, directly used, or used after digestion with a restriction enzyme when desired, or addition of a linker. The polynucleotide may have ATG as a translation initiation codon on the 5' terminal side, and may have TAA, TGA or TAG as a translation stop codon on the 3' terminal side. These translation initiation codon and translation stop codon can be added using a suitable synthesized DNA adapter.

The polynucleotide of the present invention is preferably isolated or purified. The isolated or purified polynucleotide of the present invention has a purity (ratio of the weight of the polynucleotide of the present invention to the total polynucleotide weight) of generally 50% or more, preferably 70% or more, more preferably 90% or more, most preferably 95% or more (e.g., substantially 100%).

The present invention provides a vector comprising the above-mentioned polynucleotide of the present invention. The vector of the present invention encompasses a vector comprising a polynucleotide comprising a nucleotide sequence encoding both the heavy chain variable region and the light chain variable region of the antibody of the present invention, and a combination of a vector comprising a polynucleotide comprising a nucleotide sequence encoding the heavy chain variable region so of the antibody of the present invention and a vector comprising a polynucleotide comprising a nucleotide sequence encoding the light chain variable region of the antibody of the present invention. The vector is preferably isolated or purified. Examples of the vector include expression vector, cloning vector and the like, which can be selected according to the object. Preferably, the vector is an expression vector. The expression vector can express the antibody of the present invention. The expression vector can be produced by operably linking the polynucleotide of the present invention to the downstream of a promoter in a suitable expression vector. The kind of the vector includes, for example, plasmid vector, virus vector and the like, which can be appropriately selected according to the host to be used.

As the host, the genus *Escherichia* (*Escherichia coli* etc.), the genus *Bacillus* (*Bacillus subtilis* etc), yeast (*Saccharomyces cerevisiae* etc.), insect cell (established cell line derived from larva of *Mamestra brassicae* (*Spodoptera frugiperda* cell; Sfcell) etc.), insect (larva of *Bombyx mori* etc.), mammalian cells (rat nerve cell, monkey cell (COS-7 etc.), Chinese hamster cell (CHO cell etc.) etc.) and the like are used.

Examples of the mammal include, but are not limited to, experiment animals such as rodents such as mouse, rat, hamster and guinea pig and the like, rabbit and the like, domestic animals such as swine, bovine, goat, horse, sheep, mink and the like, companion animals such as dog, cat and the like, primates such as human, monkey, *Macaca fascicularis, Macaca mulatta*, marmoset, orangutan, chimpanzee and the like, and the like.

Examples of the plasmid vector include plasmid vectors derived from *Escherichia coli* (e.g., pBR322, pBR325, pUC12, pUC13), plasmid vectors derived from *Bacillus subtilis* (e.g., pUB110, pTP5, pCl94), plasmid vectors derived from yeast (e.g., pSH19, pSH15) and the like, which can be appropriately selected according to the kind of the host to be used and the object of use.

The kind of the virus vector can be appropriately selected according to the kind of the host to be used and object of use. For example, when an insect cell used as a host, baculovirus vector and the like can be used. When a mammalian cell is used as a host, retrovirus vectors such as moloney murine leukemia virus vector, lentivirus vector, sindbis virus vector and the like, adenovirus vector, herpes virus vector, adeno-associated virus vector, parvovirus vector, vaccinia virus vector, sendai virus vector and the like can be used.

The promoter can be selected according to the kind of the host to be used, and one capable of initiating transcription in the host can be selected. For example, when the host is the genus *Escherichia*, trp promoter, lac promoter, T7 promoter and the like are preferable. When the host is the genus *Bacillus*, SPO1 promoter, SPO2 promoter, penP promoter and the like are preferable. When the host is yeast, PHO5 promoter, PGK promoter and the like are preferable. When the host is an insect cell, polyhedrin promoter, P10 promoter and the like are preferable. When the host is a mammalian cell, subgenomic (26S) promoter, CMV promoter, SRα promoter and the like are preferable.

The vector of the present invention may contain a signal sequence for antibody secretion. As the signal sequence for antibody secretion when it is produced in the periplasm of *Escherichia coli*, pelB signal sequence (Lei, S. P. et al J. Bacteriol. (1987) 169, 4379) may be used.

When desired, the vector of the present invention may contain enhancer, splicing signal, polyA addition signal, selection marker, SV40 replication origin (hereinafter sometimes to be abbreviated as SV40ori) and the like each in an operable manner. Examples of the selection marker include dihydrofolate reductase (hereinafter sometimes to be abbreviated as dhfr) gene [methotrexate (MTX) resistance], ampicillin resistance gene (sometimes to be abbreviated as $Amp^r$), neomycin resistance gene (sometimes to be abbreviated as $Neo^r$, G418 resistance) and the like.

By introducing the above-mentioned vector of the present invention into the above-mentioned host by gene transfer methods known per se (e.g., lipofection method, calcium phosphate method, microinjection method, proplast fusion method, electroporation method, DEAE dextran method, gene transfer method by Gene Gun etc.), a transformant with the vector introduced thereinto (transformant of the present invention) can be produced. When an expression vector is used as the vector to be introduced, the transformant can express the antibody of the present invention. The transformant of the present invention is useful for the production of the antibody of the present invention and the like.

The antibody of the present invention can be produced by culturing the transformant of the present invention by a method known per se according to the kind of the host, and isolating the antibody of the present invention from the culture. When the host is the genus *Escherichia*, the transformant is cultured in an appropriate medium such as LB medium, M9 medium and the like at generally about 15-43° C. for about 3-24 hr. When the host is the genus *Bacillus*, the transformant is cultured in an appropriate medium generally at about 30-40° C. for about 6-24 hr. When the host is yeast, the transformant is cultured in an appropriate medium such as Burkholder's medium and the like generally at about 20° C.-35° C. for about 24-72 hr. When the host is an insect cell or insect, the transformant is cultured in an appropriate medium such as Grace's insect medium added with about 10% of bovine serum and the like generally at about 27° C. for about 3-5 days. When the host is an animal cell, the transformant is cultured in an appropriate medium such as MEM medium added with about 10% of bovine serum and the like generally at about 30° C.-40° C. for about 15-60 hr. In any culture, aeration and stirring may be performed as necessary.

As for the production method of antibody by genetic engineering, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137 and the like can be referred to.

The separation and purification of the antibody of the present invention from a culture is not limited in any manner, and the separation and purification methods generally used for purification of antibody can be employed. For example, antibody can be separated and purified by appropriately selecting and combining chromatography column, filter, ultrafiltration, salting cut, solvent precipitation, solvent extraction, distillation, immunoprecipitation, SDS-polyacryiamide gel electrophoresis, isoelectric focusing, dialysis, recrystallization and the like.

Examples of the chromatography include affinity chromatography, ion exchange chromatography, hydrophobic chromatography, gelfiltration, reversed-phase chromatography, adsorption chromatography and the like (Strategies for Protein Purification and Characterization: A Laboratory Course Manual. Ed Daniel R. Marshak et al., Cold Spring Harbor Laboratory Press, 1996). These chromatographys can be performed by using liquid phase chromatography, for example, liquid phase chromatography such as HPLC, FPLC and the like. Examples of the column to be used for affinity chromatography include protein A column and protein G column. For example, as a column using protein A, Hyper D, POROS, Sepharose FF (manufactured by GE Amersham Biosciences) and the like can be mentioned. The present invention also encompasses an antibody highly purified by these purification methods.

In addition, the present invention provides a pharmaceutical composition containing the above-mentioned antibody of the present invention as an active ingredient. The pharmaceutical composition of the present invention can also be used for the prophylaxis or treatment of allergic diseases and inflammatory diseases involving human CD69. That is, the present invention also provides a prophylactic agent or a therapeutic agent for allergic diseases or inflammatory diseases, which contains the aforementioned antibody as an active ingredient. Examples of the allergic disease include, but are not limited to, allergic asthma, allergic rhinitis, pollinosis, atopic dermatitis, urticaria, food allergy, allergic conjunctivitis, and the like. Examples of the inflammatory disease include, but are not limited to, chronic obstructive pulmonary disease (COPD), emphysema, bronchitis, interstitial pneumonia, lung fibrosis, lung edema, adult respiratory distress syndrome, rheumatoid arthritis, septic shock, ulcerative colitis, Crohn's disease, reperfusion damage, chronic glomerulonephritis, endotoxin shock, osteoarthritis, multiple sclerosis and the like. The above-mentioned allergic disease or inflammatory disease is preferably an allergic so disease or inflammatory disease in the respiratory organs (lung, bronchus, airway etc.). Examples of the allergic disease in the respiratory organs (lung, bronchus, airway etc.) include, but are not limited to, allergic asthma and the like. Examples of the inflammatory disease in the respiratory organs (lung, bronchus, airway etc.) include, but are not limited to, chronic obstructive pulmonary disease (COPD), emphysema, bronchitis, interstitial pneumonia, lung fibrosis, lung edema, adult respiratory distress syndrome and the like.

When the antibody of the present invention is "contained as an active ingredient", it means that the antibody of the present invention is contained as at least one of the active ingredients, and does not limit the content thereof. The pharmaceutical composition of the present invention may contain other active ingredient (s) together with the antibody of the present invention.

The antibody of the present invention can be formulated according to a conventional method (e.g., Remington's Pharmaceutical Science, latest edition, Mark Publishing Company, Easton, U.S.A.). Where necessary, moreover, it may contain a pharmaceutically acceptable carrier and/or additive. For example, it can contain surfactant (PEG, Tween etc.), excipient, antioxidant (ascorbic acid etc.), colorant, flavor, preservative, stabilizer, buffering agent (phosphate, citrate, other organic acid etc.), chelating agent (EDTA etc.), suspending agent, isotonizing agent, binder, disintegrant, lubricant, glidant, corrigent and the like. Not being limited to these, the pharmaceutical composition of the present invention may contain other conventional carriers as appropriate. Specific examples include light anhydrous silicic acid, lactose, crystalline cellulose, mannitol, starch, carmellose calcium, carmellose sodium, hydroxypropylcellulose, hydroxypropylmethylcellulose, polyvinyl acetaldiethylaminoacetate, polyvinylpyrrolidone, gelatin, medium-chain fatty acid triglyceride, polyoxyethylene hydrogenated castor oil 60, sucrose, carboxymethylcellulose, cornstarch, inorganic salts and the like. It may also contain other low-molecular-weight polypeptide, serum albumin, gelatin and protein such as immunoglobulin and the like, as well as amino acid. When an aqueous solution for injection is formulated, the antibody of the present invention is dissolved in, for example, isotonic solution containing saline, glucose or other auxiliary agent. Examples of the auxiliary agent include D-sorbitol, D-mannose, D-mannitol, and sodium chloride, and may be used in combination with suitable solubilizing agents, for example, alcohol (ethanol etc.), polyalcohol (propylene glycol, PEG etc.), non-ionic surfactant (polysorbate80, HCO-50) and the like.

Where necessary, polypeptide may also be included in a microcapsule (microcapsules made of hydxoxymethylcellulose, gelatin, poly[methylmethacrylate] and the like), or formulated as a colloid drug delivery system (liposome, albumin microsphere, microemulsion, nanoparticles and nanocapsule etc.) (see Remington's Pharmaceutical Science 16th edition &, Oslo Ed. (1980) etc.). Furthermore, a method of formulating a drug as a sustained-release medicament is also known, and applicable to polypeptide (Langer et al., J. Biomed. Mater. Res. (1981)15: 167-277; Langer, Chem. Tech. (1982)12: 98-105; U.S. Pat. No. 3,773,919; EP-A-58,481; Sidman et al., Biopolymers (1983) 22: 547-56; EP No. 133,988). Furthermore, it is also possible to increase the liquid amount to be subcutaneously administered by adding or blending hyaluronidase to or with the present agent (e.g., WO 2004/078140 etc.).

The content of the antibody of the present invention in a pharmaceutical composition is, for example, about 0.01-100 wt %, preferably 0.1-99.9 wt %, of the whole pharmaceutical composition.

While the pharmaceutical composition of the present invention can be administered both orally and parenterally, it is preferably administered parenterally. Specifically, it is administered to patients by injection or transdermal administration. As an example of the dosage form of injection, it can be administered systemically or topically by intravenously injection, intramuscular injection, subcutaneous injection and the like. It may also be administered to the treatment site or in the vicinity thereof by topical injection, particularly intramuscular injection. Examples of the dosage form of transdermal administration include ointment, gel, cream, plaster, patch and the like, which can be administered systemically or topically. In addition, the administration method can be appropriately selected according to the age and symptom of the patients. The dose can be selected from, for example, the range of 0.5 mg-2.5 mg/kg body weight as the antibody of the present, invention. However, the pharmaceutical composition of the present invention is not limited by these doses.

The present invention provides a non-human mammal useful for the analysis of the function of human CD69 in allergic diseases, inflammatory diseases and the like. Specifically, the present invention provides a non-human mammal comprising a transferred Th2 cells of OD69 deficient, non-human mammal immunized with a particular antigen, which express human CD69.

Examples of the non-human mammal include experiment animals such as mouse, rat, hamster, guinea pig, rabbit and the like, domestic animals such as swine, bovine, goat, horse, sheep and the like, pets such as dog, cat and the like, primates such as monkey, orangutan, chimpanzee and the like. The non-human mammal is preferably mouse.

The genotype of the CD69 deficient non-human mammal, from which the Th2 cells are derived, may be immunologically self (i.e., syngenic) or immunologically nonself (i.e., allogeneic or xenogeneic) to the animal species of the non-human mammal of the present invention. Since the transferred Th2 cells are engrafted in the body for a long term, it is preferably immunologically self.

Being CD69 deficient refers to the state where sufficient operation of the normal function that CD69 gene intrinsically has is prevented. Examples thereof include a complete absence of the expression of CD69 gene, a decreased expression level at which the normal function that CD69 gene intrinsically has cannot be exhibited sufficiently, complete loss of the function of CD69 gene product, and a decreased function of CD69 gene product at which the normal function that CD69 gene intrinsically has cannot be exhibited.

The CD69 deficient non-human mammal is preferably an animal accompanying modification of genome DNA, i.e., transgenic animal. The CD69 deficient non-human mammal may be CD69 gene deficient heterozygote, or CD69 gene deficient homozygote, preferably CD69 gene deficient homozygote.

A CD69 deficient non-human mammal can be obtained by, for example, transfecting ES cells with a targeting vector inducing homologous recombination of CD69 gene to prepare ES cells introduced with deficiency in one of the alleles of CD69 gene, preparing, from the obtained ES cells, offspring animals introduced with deficiency in one of the alleles of CD69 gene derived therefrom, and crossing the offspring animals. For the production of CD69 deficient mouse, for example, Murata, K. et al. 2003. Int. Immunol. 15: 987-992 can be referred to.

The kind of the antigen is not particularly limited as long as it has antigenicity to the CD69 deficient non-human mammal, and a desired antigen can be selected. Examples of the antigen include protein, peptide, lipid, sugar chain and the like having antigenicity to the CD69 deficient non-human mammal.

The CD69 deficient non-human mammal can be immunized with an antigen by injecting the antigen in an amount sufficient for immunizing the CD69 deficient non-human mammal. For example, the CD69 deficient non-human mammal is immunized with the antigen at a frequency of once in 1-3 weeks, 2-6 times in total. For immunization, the antigen may be administered together with an adjuvant to the CD69 deficient non-human mammal. While the adjuvant is not particularly limited as long as it can enhance immunogenicity, for example, aluminum hydroxide, keyhole limpet hemocyanin, dextran, BCG, aluminum phosphate, TLR ligand (e.g., lipopolysaccharide (IPS), CpG) and the like can be mentioned. Aluminum hydroxide and the like are preferably used for efficient induction of Th2 cells.

Th2 cell refers to a CD4T cell which is differentiated from nave CD4T cells by antigen stimulation, and predominantly producing IL-4.

Th2 cells can be obtained by, for example, isolating CD4T cells from the spleen or peripheral blood of a CD69 deficient non-human mammal immunized with a particular antigen, and cultivating the CD4T cells in the presence of the antigen, antigen presenting cells, IL-2 and IL-4. An immobilized anti-TCR antibody or anti-CD3 antibody may also be used instead of the antigen. Th2 cells can be induced more potently by using an immobilized anti-CD28 antibody in combination.

Whether the obtained cells are Th2 cells can be confirmed so by stimulating the obtained cells with the antigen, and evaluating whether it predominantly produces IL-4 as compared to IFN-γ by flow cytometry.

To achieve expression of human CD69 in Th2 cells of a CD69 deficient non-human mammal, generally, Th2 cells of the CD69 deficient non-human mammal are transfected with an expression vector capable of expressing human CD69 in Th2 cells of the non-human mammal. As the vector, plasmid vector, virus vector, retrovirus vector and the like can be mentioned. When a retrovirus vector is used, transgene can be easily incorporated into the chromosome and the expression of human CD69 can be stably continued even when Th2 cells are proliferated. Thus, retrovirus vector is preferably used in the present invention. For the detail of gene transfer into Th2 cells by retrovirus, see, for example, Kimura, M. et al. 2001. Immunity 15: 275-287.

The expression of human CD69 in Th2 cell can be confirmed by flow cytometry using an anti-human CD69 antibody.

Th2 cells of a CD69 deficient non-human mammal immunized with a particular antigen, that express human CD69, can be transferred into a recipient non-human marital by intravenously or intraperitoneally injecting the Th2 cells to the recipient non-human mammal. The number of the Th2 cells to be transferred is not particularly limited as long as the response reaction of the transferred Th2 cells to said antigen can be observed in the recipient non-human mammal. When the recipient non-human mammal is a mouse, for example, 1,000,000-3,000,000 Th2 cells are preferably transferred.

The transferred Th2 cells are activated by stimulation. with the particular antigen to produce a large amount of IL-4. Therefore, when the non-human mammal of the present invention so is exposed to said antigen, an allergic reaction mediated by the Th2 cells expressing human CD69 and an inflammation reaction associated therewith occur. The present invention also provides such non-human mammal allergy model. Using the non-human mammal of the present invention, the role of human CD69 in allergic reactions and inflammation reactions can be easily analyzed in vivo. In addition, efficacy evaluation of an anti-human CD69 antibody for allergic diseases and inflammatory diseases can be performed in non-human mammals.

All references cited in the present specification, including publication, patent document and the like, are hereby incorporated individually and specifically by reference, to the extent that the entireties thereof have been specifically disclosed herein.

EXAMPLES

The present invention is explained in more detail in the following by referring to Examples, which are not to be construed as limitative. Various gene manipulations in the Examples followed the method described in Molecular cloning third. ed. (Cold Spring Harbor Lab. Press, 2001).

Example 1

Production of Antigen and Antibody (1) Production of Human CD69 Recombinant Protein Since human CD69 forms a homodimer via cysteine 68, cDNA (NM_001781) encoding the extracellular region (amino acid sequences; 62-199) containing cysteine 68 was inserted into a vector for *Escherichia coli* periplasm expression. Competent cells of *Escherichia coli* TG1F(−) strain prepared in advance (Z-competent *E. coli* Transformation Buffer Set: manufactured by ZYMO RESEARCH) were transformed with this expression vector, and cultured on a LB agar plate containing chloramphenicol (final concentration 34 µg/mL at 37° C. overnight. This *Escherichia coli* cells were inoculated in a 2×YT medium, and cultured at 37° C. for 3-5 hr (OD600=0.5-0.8). IPTG (final concentration 0.1 mM) was added, and the mixture was cultured at 25° C. overnight. The cultured *Escherichia coli* cells were collected by centrifugation, and lysed with lysis buffer (200 nM borate, 160 mM NaCl, 2 mM EDTA, 1 mg/ml lysozyme, pH 8.0), and the lysate was centrifuged to give a soluble fraction. From this soluble fraction, human CD69 homodimer protein was purified according to the standard method of Strep-Tactin column (manufactured by IBA). In addition, the purity of the purified human CD69 recombinant protein was confirmed to be not less than 95% by SDS-PAGE, and the protein concentration was determined by using BCA Protein Assay Kit (manufactured by PIERCE).

(2) Biotinylation of Human CD69 Recombinant Protein

The purified human CD69 recombinant protein was biotinylated according to the standard protocol of EZ-Link NHS-PEO$_4$-Biotin (Thermo Scientific), and the concentration was determined by using BCA Protein Assay Kit (manufactured by PIERCE).

(3) Selection of Human CD69 Specific Antibody Clone by Phage Display Method

The biotinylated human CD69 recombinant protein was immobilized on streptavidin-coated magnetic beads (Dynabeads MyOne Streptavidin T1 magnetic beads, manufactured by invitrogen, 100 µl) at 4° C. for 1 hr, and washed 5 times with 1 ml PBST (PBS containing 0.05% ween 20). Using HuCAL GOLD (manufactured by MorphoSys) for human antibody phage library, antibody selection was performed according to the method described in WO 2007/042309, WO 2006/122797 and the like. Human CD69-immobilized beads were added to the phage library to bind an antigen-specific antibody. The magnetic beads were recovered and washed several times, and the phage was eluted from the magnetic beads. *Escherichia coli* cells were infected with the eluted phage and cultured at 37° C. overnight. An operation of phage-rescue from the phage-infected *Escherichia coli* cells followed a general method (Molecular cloning third. Ed. Cold Spring Harbor Lab. Press, 2001). The selection round described above was repeated several times to concentrate a phage presenting an antibody specific to the antigen.

(4) Screening for Antigen-Specific Antibody by ELISA

The pool of Fab genes obtained after the concentration operation was subcloned to *Escherichia coli* expression vector. According to the method described in WO 2006/122797 and the like, the Fab antibody was expressed, and the antigen-specific antibody was screened for by the ELISA method. The Fab antibody was purified from a soluble fraction of *Escherichia coli* lysate according to the standard method of Strep-Tactin column (manufactured by IBA). In addition, the purity of the purified antibody was confirmed by SDS-PAGE, and the concentration was determined by using BCA Protein Assay Kit (manufactured by PIERCE).

(5) Screening for Antibody Clone by Cell Staining Evaluation

The purified ELISA-positive Fab antibody clones were further evaluated for antigen reactivity by cell staining of human CD69 and mouse CD69 over-expressing cells. As the antigen, CHO-S cells fixed with 4% PFA 46 hr after the transfection with human CD69 or mouse CD69 expression vector by the standard method using FreeStyle MAX Reagent (manufactured by Invitrogen) were used. With 50 µg/ml purified Fab antibody as the primary antibody for staining, cells were incubated at room temperature for 1 hr, and washed 3 times with PBS. With 500-fold diluted Alexa555-labeled anti-human IgG (manufactured by Invitrogen) as the secondary antibody, cells were incubated at room temperature for 1 hr, and washed 3 times with PBS. These cells were observed under a fluorescence microscope (IX71, manufactured by OLYMPUS), and the presence or absence of staining was evaluated. As a result, it was confirmed that 160-c76 clone binds to both human CD69 (hCD69) and mouse CD69 (mCD69) (FIG. 1), and 160-c7 and 160-c103 bind only to human CD69, and 3 clones in total were finally obtained as anti-human CD69 antibody clones that specifically bind to native-form human CD69 on the cell surface.

(6) Analysis of Base Sequence of Anti-Human CD69 Antibody Clone

The obtained three clones (160-c7, 160-c76 and 160-c103) of *Escherichia coli* were cultured, and plasmids were recovered (QIAprep Spin MiniPrep kit: manufactured by QIAGEN) and used for the base sequence analysis. Table 1 shows the amino acid sequences of CDRs (complementarity determining regions) of the respective clones.

TABLE 1

| | light chain | | |
|---|---|---|---|
| | LCDR1 | LCDR2 | LCDR3 |
| 160-c7 | RASQDISSYLN (SEQ ID NO: 1) | YGASNLQS (SEQ ID NO: 2) | QQYSDYPH (SEQ ID NO: 3) |
| 160-c76 | SGDSLGSKYVY (SEQ ID NO: 7) | VVIYGDSKRPS (SEQ ID NO: 8) | QSYDSNIM (SEQ ID NO: 9) |
| 160-c103 | RASQSVSSYLA (SEQ ID NO: 13) | YGTSIRAT (SEQ ID NO: 14) | QQEYSSPP (SEQ ID NO: 15) |

| | heavy chain | | |
|---|---|---|---|
| | HCDR1 | HCDR2 | HCDR3 |
| 160-c7 | YTFTSYDMH (SEQ ID NO: 4) | WINPYSGNTNYAQKFQG (SEQ ID NO: 5) | MYYDKDYLSWGTDS (SEQ ID NO: 6) |
| 160-c76 | FTFSNFVMH (SEQ ID NO: 10) | SISGSSSSTYYADSVKG (SEQ ID NO: 11) | YYYASFDY (SEQ ID NO: 12) |
| 160-c103 | FTFSNYYMS (SEQ ID NO: 16) | VISYDGISTHYADSVKG (SEQ ID NO: 17) | YIGNSLYMDF (SEQ ID NO: 18) |

(7) Production of IgG Antibody of Anti-Human CD69 Antibody Clones

Fab antibody genes of the obtained 3 clones were subcloned to construct IgG expression vectors (constant region of heavy chain was IgG4). HEK293T cells were transfected with these expression vectors according to the standard method of Lipofectamine (manufactured by Invitrogen), and the culture supernatant after culture for 72 hr was recovered. As the medium, DMEM (Sigma) supplemented with 10% Ultra Low IgG FBS (manufactured by invitrogen) was used. From the culture supernatant, IgG antibody was purified by the standard method using rProteinA Sepharose Fast Flow (manufactured by GE healthcare). Protein after purification was confirmed to show a single band by SDS-PAGE, and the concentration was determined by using BCA Protein Assay Kit (manufactured by PIERCE).

Example 2

Figure 2:
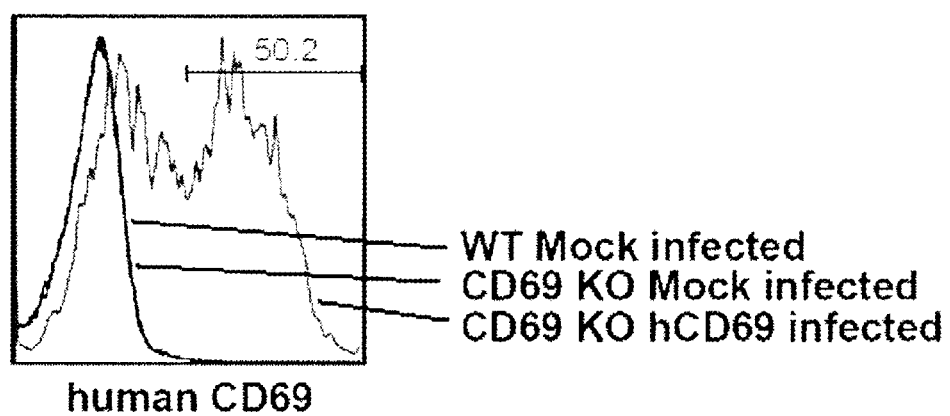
FIG. 2 shows analysis of human CD69 expression by flow cytometry.

Effect of Anti-Human CD69 Antibody on Intraalveolar Mononuclear Cell Infiltration Mice obtained by crossing BALB/c mouse or CD69 deficient (CD69KO) mouse back-crossed not less than 10 times onto BALB/c (Murata, K. et al. 2003. Int. Immunol. 15: 987-992) with DO11.10 transgenic mouse were used. The spleen CD4T cells of these mice were purified by AutoMACS sorter (Miltenyi Biotec) to a purity of >98%. The isolated CD4T cells were cultured with stimulation with immobilized anti-TCR and anti-CD28 monoclonal antibodies under Th2 conditions (IL-2 10 u/ml, IL-4 100 U/ml). Two days after the start of the culture, and human. CD69 gene was introduced by a retrovirus vector containing human CD69 (hCD69) gene. The method of introducing human CD69 gene followed the method described previously (Kimura, M. et. al. 2001. Immunity 15: 275-287). Five days after the start of the culture, the cultured cells were recovered, and the expression of human CD69 was confirmed by flow cytometry (FIG. 2). 50.2% of the cells were human CD69 positive.

3,000,000 cells of CD69 KO mouse Th2 cells that overexpress human CD69 (hCD69) obtained by the above-mentioned culture, or wild-type BALB/c mouse Th2 cells were intravenously injected into wild-type BALB/c mice (day 0). After cell transfer, on day 1 and day 3, the mice were exposed to allergen challenge via airway by inhaling 1% OVA solution in aerosolized saline for 30 min using an ultrasonication nebulizer (NE-U07; manufactured by Omron).

On day 1, 2 hr before OVA inhalation, the following antibodies were intraperitoneally injected at a dose of 100 µg/mouse:

control antibody (anti-"TSLYKKAG" peptide, IgG4, self-developed)

mouse anti-human CD69 monoclonal antibody (FN50 manufactured by BioLegend)

160-c7

160-c76

160-c103

On day 5, according to the report described previously, bronchoalveolar lavage (BAL) was performed (Kamata, T. et al., 2003, J. Clin. Invest. 111: 109-119). All bronchoalveolar lavage was collected, and the cells in 150 µl of the fractionated liquid were counted. Viable PAL cells (100,000 cells) were cytocentrifuged onto a slide by Cytospin 4 (manufactured by Thermo Fisher Scientific), and stained with May-Gruenwald Giemsa solution (manufactured by Merck). 500 leukocytes were counted on each slide, and the type was identified using the morphological criteria. The percentage of each cell type was calculated.

Figure 3:
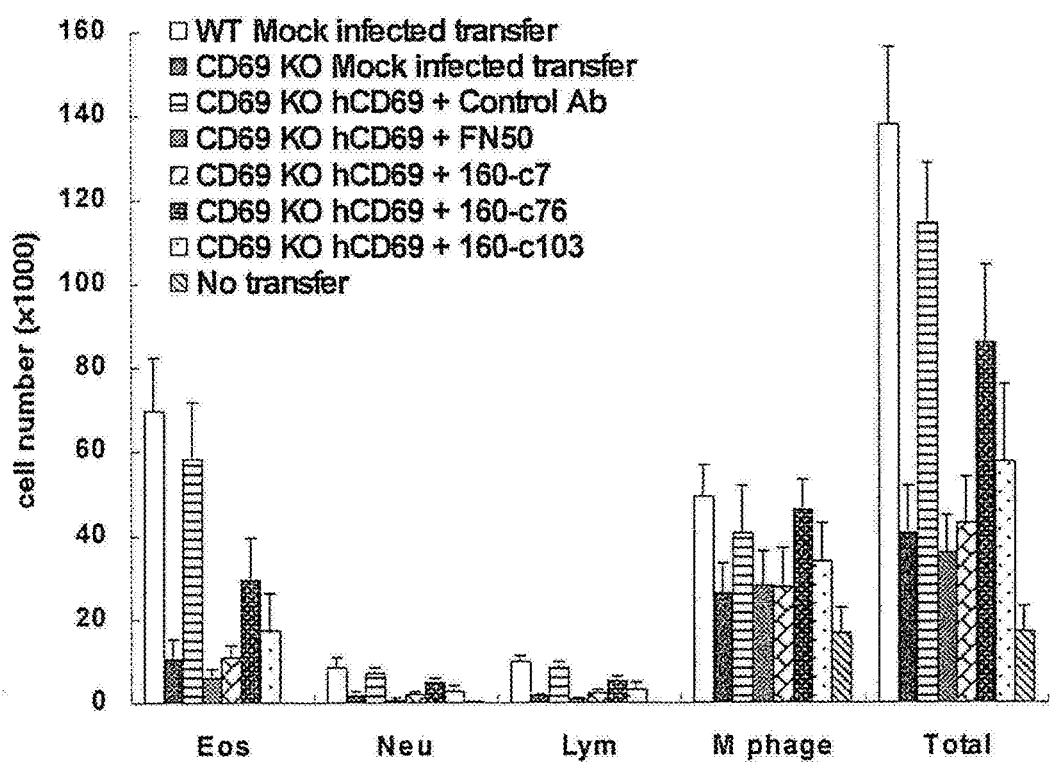
FIG. 3 shows the effect of various anti-human CD69 antibodies on alveolar leukocyte infiltration.

The results are shown in FIG. 3. The anti-hCD69 antibodies suppressed intraalveolar infiltration of mononuclear cells, particularly infiltration of eosinophils, which is caused by OVA inhalation.

Example 3

Selection of High Affinity Anti-Human CD69 Antibody

Selection of an antibody having higher affinity for human CD69 was tried by introducing a mutation into the light chain CDR3 of the antibodies selected in Example 1. To be specific, the methods described in Prassler J, Steidl S, Urlinger S. Immunotherapy. 2009 July; 1(4):571-83. and Hillig B C, Urlinger S, Fanghanel J, Brooks B, Haenel C, Stark Y, Sulzle D, Svergun D I, Baesler S, Malawski G, Moosmayer D, Menrad A, Schirner M, Licha K. J Mol Biol. 2008 Mar. 14; 377(1):206-19 were employed. The antibody selection round was repeated twice, the base sequences of the light chain CDR3 of the obtained antibody clones were examined and antibody clones having a novel sequence were identified. They were expressed in Escherichia coli, and ELISA was performed for the antigen by using the lysate and the amount of the antibody in the lysate was simultaneously measured by sandwich ELISA. The relative specific binding activity of each clone was calculated from the absorbance of ELISA against the antigen and the antibody amount, and high affinity clones were selected. In addition, IgG of top 10 clones having high affinity were prepared and $K_D$ values were measured.

In the same manner as in Example 1, Fab antibody gene was subcloned to construct IgG expression vector (constant region of heavy chain was IgG4). HEK293T cells were transfected with the expression vector by Lipofectamine (manufactured by invitorogen), cultured for 72 hr, and IgG antibody was purified from the recovered culture supernatant.

The affinity of the prepared IgG clones for human CD69 was evaluated by scatchard plot. To be specific, it was calculated according to the principle described in immunoassays (OXFORD UNIVERSITY PRESS, 2000). An antibody was incubated with various concentrations of antigen at room temperature for 2 hr until it reaches equilibrium, and the amount of free antibody present in the incubation liquids was measured by the ELISA method. The binding constant and dissociation constant ($K_D$ value) were determined based on the changes in the amount of free antibody in each equilibrate sample. The concentration of the antibody in the equilibration reaction was set to 0.015 µg/ml, and an ELISA plate immobilized with the antigen at 1 µg/ml was used for the measurement of the amount of free antibody.

As a result, a plurality of high affinity clones which bind to human CD69 while maintaining the cross-reactivity with mouse CD69 were selected from clones with the same CDRs as 160-c76 other than light chain CDR3. Table 2 shows the amino acid sequences of light chain CDR3 and affinity of two clones, 234-61 and 234-83, that showed particularly high affinity for human CD69. The affinity of these two clones for human CD69 increased to 9-fold or more that of 160-c76 clone having the same sequence other than light chain CDR3.

TABLE 2

| clone | $K_D$ (M) | cross-reactivity with mCD69 | LCDR3 |
| --- | --- | --- | --- |
| 160-c7 | 4.76E-08 | - | QQYSDYPH (SEQ ID NO: 3) |
| 160-c103 | 7.58E-09 | - | QQEYSSPP (SEQ ID NO: 15) |
| 160-c76 | 2.78E-08 | ++ | QSYDSNIM (SEQ ID NO: 9) |
| 234-61 | 1.13E-09 | + | QSYTSFTTKI (SEQ ID NO: 19) |
| 234-83 | 2.83E-09 | +++ | GSYTTGAKSH (SEQ ID NO: 20) |

Example 4

Cross-Reactivity with Mouse CD69

The reactivity with mouse CD69 was evaluated as follows. Splenocytes were isolated from wild-type mouse and CD69 KO mouse (both Balb/c), and stimulated with Phorbol 12-myristate 13-acetate (PMA) for 4 hr to induce expression of CD69 on the cell surface. Each anti-human CD69 antibody (160-c76, 234-61 and 234-83) (1 µg) was added to $1 \times 10^6$ splenocytes, and the mixture was incubated on ice for 30 min. The cells were washed, anti-human IgG-Alexa488 (×200 diluted) was added as a secondary antibody, and the mixture was incubated on ice for 20 min. After washing the cells, the intensity of staining with each anti-human CD69 antibody was evaluated by flow cytometry (FACS Calibur: manufactured by Becton, Dickinson). As a positive control, hamster anti-mouse CD69 monoclonal antibody (H1.2F3)-FITC (manufactured by Becton, Dickinson) was used.

On the other hand, the reactivity with human CD69 was evaluated in the same manner as for mouse CD69 by using peripheral blood mononuclear cells (PBMCs) of a healthy subject, which were induced to express CD69 on the cell surface by stimulating with PMA for 4 hr. As a positive control, mouse anti-human CD69 monoclonal antibody (FN50) (manufactured by BioLegend) was used.

Figure 4:
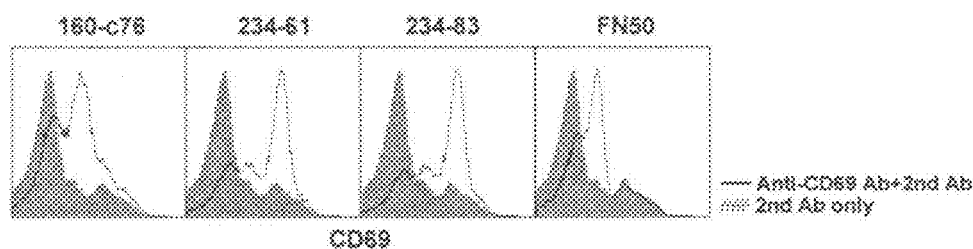
FIG. 4 confirms cross-reactivity of various anti-human. CD69 antibodies with mouse CD69 and human CD69 by flow cytometry.
Figure 4:
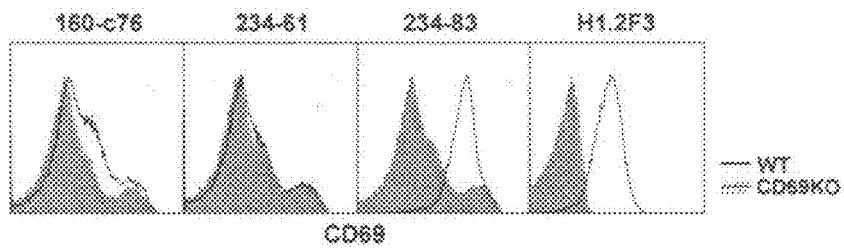

As a result, all 160-c76, 234-61 and 234-83 clones bound to activated mouse splenocytes and activated human peripheral blood mononuclear cells, and cross-reaction with both mouse CD69 (mCD69) and human CD69 (hCD69) was observed (FIG. 4). As compared to 160-c76, the intensity of staining of mouse CD69 by 234-61 was weak. On the other hand, 234-83 strongly bound to mouse CD69.

Example 5

Effect of Anti-Human CD69 Antibody on Intraalveolar Mononuclear Infiltration The effect of the following anti-human CD69 antibodies on intraalveolar mononuclear infiltration was evaluated according to a similar protocol as in Example 2.

control antibody (anti-"TSLYKKG" peptide, IgG4, self-developed)
mouse anti-human CD69 mnoclonal antibody (FN50 manufactured by BioLegend)
160-c76
234-61
234-83

CD69 deficient (CD69 KO) mice back-crossed not less than 10 times onto BALB/c were intraperitoneally immunized with 250 µg of OVA (hen egg albumin from Sigma-Aldrich) in 4 mg of aluminum hydroxide gel (alum). Spleen CD4T cells of the OVA-immunized CD69 deficient mouse were purified using CD4+T cell isolation kit manufactured by Miltenyi Biotec) and AutoMACS sorter (manufactured by Miltenyi Biotec) to a purity of >98%. The isolated CD4T cells were cultured with stimulating with immobilized anti-TCR and anti-CD28 mAbs under Th2 conditions. Two days after the start of the culture, hCD69 gene was introduced by a retrovirus vector containing human CD69 (hCD69) gene. Five days after the start of the culture, the cultured cells were recovered, and the expression of hCD69 was confirmed by flow cytometry. 58.7% of the cells were hCD69 positive.

3,000,000 cells of CD69 KO mouse Th2 cells that overexpress hCD69 obtained by the above-mentioned culture, or wild-type BALB/c mouse Th2 cells were intravenously injected into wild-type BALIB/c mice (day 0). After cell transfer, on day 1 and day 3, the mice were exposed to allergen challenge via airway by inhaling 1% OVA solution in aerosolized saline for 30 min using an ultrasonication nebulizer (NE-U07; manufactured by Omron).

On day 1, 2 hr before OVA inhalation, the evaluation target antibodies were intraperitoneally injected at a dose of 100 µg/mouse. On day 4, according to the report described previously, bronchoalveolar lavage (BAL) was performed (Kamata, T. et al., 2003, J. Clin. Invest. 111: 109-119). All bronchoalveolar lavage was collected, and the cells in 150 µl of the fractionated liquid were counted. Viable BAL cells (100,000 cells) were centrifuged onto a slide by Cytospin 4 (manufactured by Thermo Fisher Scientific), and stained with May-Gruenwald Giemsa solution (manufactured by Merck). 500 leukocytes were counted on each slide, and the cell type was identified using the morphological criteria. The percentage of each cell type was calculated.

Figure 5:
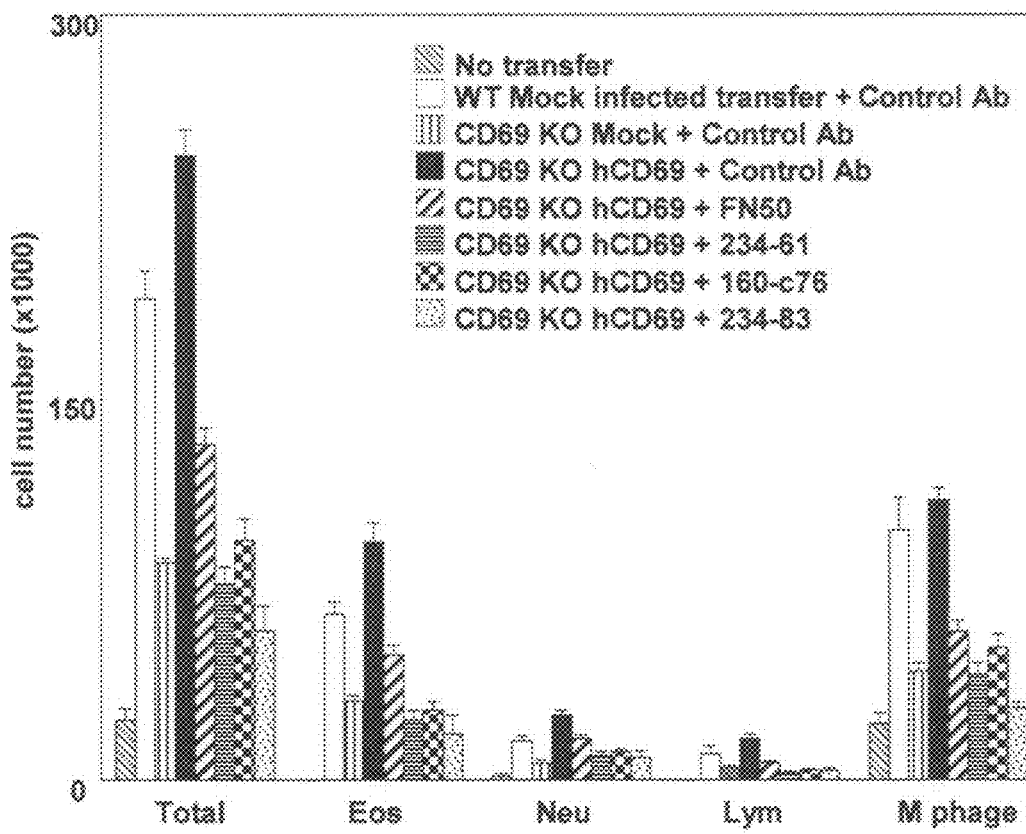
FIG. 5 shows the effect of various anti-human CD69 antibodies against alveolar leukocyte infiltration.

The results are shown in FIG. 5. All evaluated anti-hCD69 antibody suppressed intraalveolar infiltration of leukocytes (eosinophils, neutrophils, lymphocytes, macrophages) caused by OVA inhalation. The leukocyte infiltration suppressing capacity was FN50<160-c76<234-61<234-83, whereby enhancement of leukocyte infiltration suppressing capacity by affinity improvement was confirmed.

Example 6

Identification of Epitope

Using a peptide array on which partial peptides of human CD69 were immobilized, epitope mapping of anti-human CD69 antibodies 234-83, 160-c7 and 160-c103 was performed. To be specific, as shown in the following Table, a peptide array consisting of peptides having the residue number of 12 amino acid residues and an offset of 3 amino acid residues was produced for a sequence covering the extracellular domain of human CD69 (60-199) (PepSpots, manufactured by JPT). The peptide array and the anti-human CD69 antibody were reacted according to the manual of JPT. Anti-human CD69 antibodies labeled with HRP (Peroxidase Labeling Kit—NH2, manufactured by Dojindo) were used.

TABLE 3

| | | | | | |
|---|---|---|---|---|---|
| 1 | ALSVGQYNCPGQ (SEQ ID NO: 34) | 16 | SWTSAQNACSEH (SEQ ID NO: 49) | 31 | GHPWKWSNGKEF (SEQ ID NO: 64) |
| 2 | VGQYNCPGQYTF (SEQ ID NO: 35) | 17 | SAQNACSEHGAT (SEQ ID NO: 50) | 32 | WKWSNGKEFNNW (SEQ ID NO: 65) |
| 3 | YNCPGQYTFSMP (SEQ ID NO: 36) | 18 | NACSEHGATLAV (SEQ ID NO: 51) | 33 | SNGKEFNNWFNV (SEQ ID NO: 66) |
| 4 | PGQYTFSMPSDS (SEQ ID NO: 37) | 19 | SEHGATLAVIDS (SEQ ID NO: 52) | 34 | KEFNNWFNVTGS (SEQ ID NO: 67) |
| 5 | YTFSMPSDSHVS (SEQ ID NO: 38) | 20 | GATLAVIDSEKD (SEQ ID NO: 53) | 35 | NNWFNVTGSDKC (SEQ ID NO: 68) |
| 6 | SMPSDSHVSSCS (SEQ ID NO: 39) | 21 | LAVIDSEKDMNF (SEQ ID NO: 54) | 36 | FNVTGSDKCVFL (SEQ ID NO: 69) |
| 7 | SDSHVSSCSEDW (SEQ ID NO: 40) | 22 | IDSEKDMNFLKR (SEQ ID NO: 55) | 37 | TGSDKCVFLKNT (SEQ ID NO: 70) |
| 8 | HVSSCSEDWVGY (SEQ ID NO: 41) | 23 | EKDMNFLKRYAG (SEQ ID NO: 56) | 38 | DKCVFLKNTEVS (SEQ ID NO: 71) |
| 9 | SCSEDWVGYQRK (SEQ ID NO: 42) | 24 | MNFLKRYAGREE (SEQ ID NO: 57) | 39 | VFLKNTEVSSME (SEQ ID NO: 72) |
| 10 | EDWVGYQRKCYF (SEQ ID NO: 43) | 25 | LKRYAGREEHWV (SEQ ID NO: 58) | 40 | KNTEVSSMECEK (SEQ ID NO: 73) |
| 11 | VGYQRKCYFIST (SEQ ID NO: 44) | 26 | YAGREEHWVGLK (SEQ ID NO: 59) | 41 | EVSSMECEKNLY (SEQ ID NO: 74) |
| 12 | QRKCYFISTVKR (SEQ ID NO: 45) | 27 | REEHWVGLKKEP (SEQ ID NO: 60) | 42 | SMECEKNLYWIC (SEQ ID NO: 75) |

TABLE 3-continued

| | | | | | |
|---|---|---|---|---|---|
| 13 | CYFISTVKRSWT (SEQ ID NO: 46) | 28 | HWVGLKKEPGHP (SEQ ID NO: 61) | 43 | CEKNLYWICNKP (SEQ ID NO: 76) |
| 14 | ISTVDRSWTSAQ (SEQ ID NO: 47) | 29 | GLKKEPGHPWKW (SEQ ID NO: 62) | 44 | KNLYWICNKPYK (SEQ ID NO: 77) |
| 15 | VKRSWTSAQNAC (SEQ ID NO: 48) | 30 | KEPGHPWKWSNG (SEQ ID NO: 63) | | |

As a result, 234-83 specifically bound to the above-mentioned peptides #2 and #3, particularly strongly bound to peptide #3. The results suggest that the epitope of 234-83 contains the amino acid sequence shown in SEQ ID NO: 33 (YNCPG) which is common to peptide #2 and peptide #3, and to human CD69 and mouse CD69 (FIG. 6).

160-c7 specifically bound to the above-mentioned peptide #26. The results show that 160-c7 binds to human CD69 at an epitope consisting of the amino acid sequence shown in SEQ ID NO: 59.

160-c103 specifically bound to the above-mentioned peptides #24, #25 and #26. The results suggest that the epitope of 160-c103 contains the amino acid sequence shown in SEQ ID NO: 78 (YAGREE) which is common to peptides #24, #25 and #26.

INDUSTRIAL APPLICABILITY

According to the present invention, an anti-human CD69 antibody applicable to the prophylaxis or treatment of allergic diseases and inflammatory diseases is provided. According to the present invention, moreover, an animal model permitting in vivo evaluation of a pharmacological effect of an anti-human CD69 antibody can be provided.

This application is based on a patent application No. 2012-098243 filed in Japan (filing date: Apr. 23, 2012), the contents of which are incorporated in full herein.

The invention claimed is:

1. An antibody comprising a light chain variable region and a heavy chain variable region,
   wherein the antibody binds to an epitope of the human CD69,
   wherein the light chain variable region comprises: CDR1 comprising the amino acid sequence of SEQ ID NO: 7; CDR2 comprising the amino acid sequence of SEQ ID NO: 8; and CDR3 comprising the amino acid sequence of SEQ ID NO: 9, 19 or 20, and
   wherein the heavy chain variable region comprises: CDR1 comprising the amino acid sequence of SEQ ID NO: 10; CDR2 comprising the amino acid sequence of SEQ ID NO: 11; and CDR3 comprising the amino acid sequence of SEQ ID NO: 12.

2. The antibody according to claim 1, wherein the antibody cross-reacts with mouse CD69.

3. The antibody according to claim 1,
   wherein the light chain variable region comprises the amino acid sequence of SEQ ID NO: 23, 27 or 28, and
   wherein the heavy chain variable region comprises the amino acid sequence of SEQ ID NO: 24.

4. The antibody according to claim 1, wherein the epitope comprises the amino acid sequence of SEQ ID NO: 33 and is less than or equal to 12 amino acid residues.

5. The antibody according to claim 4, wherein the epitope is a continuous partial sequence of the amino acid sequence of SEQ ID NO: 30.

6. The antibody according to claim 4, wherein the epitope consists of the amino acid sequence of SEQ ID NO: 35 or 36.

7. An antibody comprising a light chain variable region and a heavy chain variable region,
   wherein the antibody binds to an epitope of the human CD69,
   wherein the light chain variable region comprises: CDR1 comprising the amino acid sequence of SEQ ID NO: 7; CDR2 comprising the amino acid sequence of SEQ ID NO: 8; and CDR3 comprising the amino acid sequence of SEQ ID NO: 9, 19 or 20, and
   wherein the heavy chain variable region comprises: CDR1 comprising the amino acid sequence of SEQ ID NO: 10; CDR2 comprising the amino acid sequence of SEQ ID NO: 11; and CDR3 comprising the amino acid sequence of SEQ ID NO: 12
   wherein 1 to 3 amino acid residues are substituted at 1 to 3 positions selected from the group consisting of the $1^{st}$, $4^{th}$, and $5^{th}$ positions in the amino acid sequences of SEQ ID NO: 9, 19 or 20, and
   wherein the amino acid sequence of CDR3 in the light chain variable region comprises:
   glutamine or glycine at the 1st position;
   aspartic acid or threonine at the 4th position; and
   serine or threonine at the 5th position.

8. The antibody according to claim 7, wherein the amino acid sequence of the 1st position to the 5th position of CDR3 in the light chain variable region is QSYDS, QSYTS or GSYTT.

9. The antibody according to claim 7, wherein the antibody cross-reacts with mouse CD69.

10. The antibody according to claim 7, wherein the epitope comprises the amino acid sequence of SEQ ID NO: 33 and is less than or equal to 12 amino acid residues.

11. The antibody according to claim 10, wherein the epitope is a continuous partial sequence of the amino acid sequence of SEQ ID NO: 30.

12. The antibody according to claim 10, wherein the epitope consists of the amino acid sequence of SEQ ID NO: 35 or 36.

* * * * *

SEQUENCE LISTING

```
<160> NUMBER OF SEQ ID NOS: 78

<210> SEQ ID NO 1
<211> LENGTH: 11
<212> TYPE: PRT
<213> ORGANISM: Artificial Sequence
<220> FEATURE:
<223> OTHER INFORMATION: Synthetic 160-c7 LCDR1

<400> SEQUENCE: 1

Arg Ala Ser Gln Asp Ile Ser Ser Tyr Leu Asn
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic 160-c7 LCDR2

<400> SEQUENCE: 2

Tyr Gly Ala Ser Asn Leu Gln Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic 160-c7 LCDR3

<400> SEQUENCE: 3

Gln Gln Tyr Ser Asp Tyr Pro His
1               5

<210> SEQ ID NO 4
<211> LENGTH: 9
<212> TYPE: PRT
```

```
<213> ORGANISM: Artificial Sequence
<220> FEATURE:
<223> OTHER INFORMATION: Synthetic 160-c7 HCDR1

<400> SEQUENCE: 4

Tyr Thr Phe Thr Ser Tyr Asp Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic 160-c7 HCDR2

<400> SEQUENCE: 5

Trp Ile Asn Pro Tyr Ser Gly Asn Thr Asn Tyr Ala Gln Lys Phe Gln
1               5                   10                  15
Gly

<210> SEQ ID NO 6
<211> LENGTH: 14
<212> TYPE: PRT
<213> ORGANISM: Artificial Sequence
<220> FEATURE:
<223> OTHER INFORMATION: Synthetic 160-c7 HCDR3

<400> SEQUENCE: 6

Met Tyr Tyr Asp Lys Asp Tyr Leu Ser Trp Gly Thr Asp Ser
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic 160-c76  LCDR1

<400> SEQUENCE: 7

Ser Gly Asp Ser Leu Gly Ser Lys Tyr Val Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic 160-c76 LCDR2

<400> SEQUENCE: 8

Val Val Ile Tyr Gly Asp Ser Lys Arg Pro Ser
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic 160-c76 LCDR3

<400> SEQUENCE: 9

Gln Ser Tyr Asp Ser Asn Ile Met
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: Synthetic 160-c76 HCDR1

<400> SEQUENCE: 10

Phe Thr Phe Ser Asn Phe Val Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic 160-c76 HCDR2

<400> SEQUENCE: 11

Ser Ile Ser Gly Ser Ser Ser Ser Thr Tyr Tyr Ala Asp Ser Val Lys
1               5                   10                  15

Gly

<210> SEQ ID NO 12
<211> LENGTH: 8
<212> TYPE: PRT
<213> ORGANISM: Artificial Sequence
<220> FEATURE:
<223> OTHER INFORMATION: Synthetic 160-c76 HCDR3

<400> SEQUENCE: 12

Tyr Tyr Tyr Ala Ser Phe Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic 160-c103 LCDR1

<400> SEQUENCE: 13

Arg Ala Ser Gln Ser Val Ser Ser Tyr Leu Ala
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthetic 160-c103 LCDR2

<400> SEQUENCE: 14

Tyr Gly Thr Ser Ile Arg Ala Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic 160-c103 LCDR3

<400> SEQUENCE: 15

Gln Gln Glu Tyr Ser Ser Pro Pro
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Synthetic 160-c103 HCDR1

<400> SEQUENCE: 16

Phe Thr Phe Ser Asn Tyr Tyr Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic 160-c103 HCDR2

<400> SEQUENCE: 17

Val Ile Ser Tyr Asp Gly Ile Ser Thr His Tyr Ala Asp Ser Val Lys
1               5                   10                  15

Gly

<210> SEQ ID NO 18
<211> LENGTH: 10
<212> TYPE: PRT
<213> ORGANISM: Artificial Sequence
<220> FEATURE:
<223> OTHER INFORMATION: Synthetic 160-c103 HCDR3

<400> SEQUENCE: 18

Tyr Ile Gly Asn Ser Leu Tyr Met Asp Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic 234-61 LCDR3

<400> SEQUENCE: 19

Gln Ser Tyr Thr Ser Phe Thr Thr Lys Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic 234-83 LCDR3

<400> SEQUENCE: 20

Gly Ser Tyr Thr Thr Gly Ala Lys Ser His
1               5                   10

<210> SEQ ID NO 21
<211> LENGTH: 109
<212> TYPE: PRT
<213> ORGANISM: Artificial Sequence
<220> FEATURE:
<223> OTHER INFORMATION: Synthetic 160-c7 VL

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
```

```
                    20                  25                  30
Leu Asn Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Asp Tyr Pro His
                85                  90                  95

Thr Phe Gly Gln Gly Thr Lys Val Glu Ile Lys Arg Thr
            100                 105
```

<210> SEQ ID NO 22
<211> LENGTH: 123
<212> TYPE: PRT
<213> ORGANISM: Artificial Sequence
<220> FEATURE:
<223> OTHER INFORMATION: Synthetic 160-c7 VH

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Met His Trp Val Arg Gln Ala Pro Gly Gln Gly Leu Glu Trp Met
            35                  40                  45

Gly Trp Ile Asn Pro Tyr Ser Gly Asn Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Tyr Asp Lys Asp Tyr Leu Ser Trp Gly Thr Asp Ser
            100                 105                 110

Trp Gly Gln Gly Thr Leu Val Thr Val Ser Ser
        115                 120
```

<210> SEQ ID NO 23
<211> LENGTH: 107
<212> TYPE: PRT
<213> ORGANISM: Artificial Sequence
<220> FEATURE:
<223> OTHER INFORMATION: Synthetic 160-c76 VL

<400> SEQUENCE: 23

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Ser Lys Tyr Val
                20                  25                  30

Tyr Trp Tyr Gln Gln Lys Pro Gly Gln Ala Pro Val Val Ile Tyr
            35                  40                  45

Gly Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Asn Ile Met Val
                85                  90                  95
```

```
Phe Gly Gly Gly Thr Lys Leu Thr Val Leu Gly
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic 160-c76 VH

<400> SEQUENCE: 24

Gln Val Gln Pro Gly Gly Ser Leu Arg Leu Ser Cys Ala Ala Ser Gly
1               5                   10                  15

Phe Thr Phe Ser Asn Phe Val Met His Trp Val Arg Gln Ala Pro Gly
            20                  25                  30

Lys Gly Leu Glu Trp Val Ser Ser Ile Ser Gly Ser Ser Ser Ser Thr
        35                  40                  45

Tyr Tyr Ala Asp Ser Val Lys Gly Arg Phe Thr Ile Ser Arg Asp Asn
    50                  55                  60

Ser Lys Asn Thr Leu Tyr Leu Gln Met Asn Ser Leu Arg Ala Glu Asp
65                  70                  75                  80

Thr Ala Val Tyr Tyr Cys Ala Arg Tyr Tyr Tyr Ala Ser Phe Asp Tyr
                85                  90                  95

Trp Gly Gln Gly Thr Leu Val Thr Val Ser Ser
            100                 105

<210> SEQ ID NO 25
<211> LENGTH: 109
<212> TYPE: PRT
<213> ORGANISM: Artificial Sequence
<220> FEATURE:
<223> OTHER INFORMATION: Synthetic 160-c103 VL

<400> SEQUENCE: 25

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Thr Ser Ile Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Glu Tyr Ser Ser Pro Pro
                85                  90                  95

Thr Phe Gly Gln Gly Thr Lys Val Glu Ile Lys Arg Thr
            100                 105

<210> SEQ ID NO 26
<211> LENGTH: 119
<212> TYPE: PRT
<213> ORGANISM: Artificial Sequence
<220> FEATURE:
<223> OTHER INFORMATION: Synthetic 160-c103 VH

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
```

```
            20                  25                  30
Tyr Met Ser Trp Val Arg Gln Ala Pro Gly Lys Gly Leu Glu Trp Val
         35                  40                  45

Ser Val Ile Ser Tyr Asp Gly Ile Ser Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ile Gly Asn Ser Leu Tyr Met Asp Phe Trp Gly Gln Gly
            100                 105                 110

Thr Leu Val Thr Val Ser Ser
            115
```

<210> SEQ ID NO 27
<211> LENGTH: 109
<212> TYPE: PRT
<213> ORGANISM: Artificial Sequence
<220> FEATURE:
<223> OTHER INFORMATION: Synthetic 234-61 VL

<400> SEQUENCE: 27

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Gly Ser Lys Tyr Val
            20                  25                  30

Tyr Trp Tyr Gln Gln Lys Pro Gly Gln Ala Pro Val Val Val Ile Tyr
         35                  40                  45

Gly Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Thr Ser Phe Thr Thr Lys
                 85                  90                  95

Ile Val Phe Gly Gly Gly Thr Lys Leu Thr Val Leu Gly
            100                 105
```

<210> SEQ ID NO 28
<211> LENGTH: 109
<212> TYPE: PRT
<213> ORGANISM: Artificial Sequence
<220> FEATURE:
<223> OTHER INFORMATION: Synthetic 234-83 VL

<400> SEQUENCE: 28

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Gly Ser Lys Tyr Val
            20                  25                  30

Tyr Trp Tyr Gln Gln Lys Pro Gly Gln Ala Pro Val Val Val Ile Tyr
         35                  40                  45

Gly Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Thr Thr Gly Ala Lys Ser
                 85                  90                  95
```

His Val Phe Gly Gly Thr Lys Leu Thr Val Leu Gly
              100                 105

<210> SEQ ID NO 29
<211> LENGTH: 600
<212> TYPE: DNA
<213> ORGANISM: Homo sapiens
<220> FEATURE:
<221> NAME/KEY: CDS
<222> LOCATION: (1)..(600)

<400> SEQUENCE: 29

```
atg agc tct gaa aat tgt ttc gta gca gag aac agc tct ttg cat ccg      48
Met Ser Ser Glu Asn Cys Phe Val Ala Glu Asn Ser Ser Leu His Pro
1               5                   10                  15 gag agt gga caa gaa aat gat gcc acc agt ccc cat ttc tca aca cgt      96
Glu Ser Gly Gln Glu Asn Asp Ala Thr Ser Pro His Phe Ser Thr Arg
            20                  25                  30 cat gaa ggg tcc ttc caa gtt cct gtc ctg tgt gct gta atg aat gtg     144
His Glu Gly Ser Phe Gln Val Pro Val Leu Cys Ala Val Met Asn Val
        35                  40                  45 gtc ttc atc acc att tta atc ata gct ctc att gcc tta tca gtg ggc     192
Val Phe Ile Thr Ile Leu Ile Ile Ala Leu Ile Ala Leu Ser Val Gly
    50                  55                  60 caa tac aat tgt cca ggc caa tac aca ttc tca atg cca tca gac agc     240
Gln Tyr Asn Cys Pro Gly Gln Tyr Thr Phe Ser Met Pro Ser Asp Ser
65                  70                  75                  80 cat gtt tct tca tgc tct gag gac tgg gtt ggc tac cag agg aaa tgc     288
His Val Ser Ser Cys Ser Glu Asp Trp Val Gly Tyr Gln Arg Lys Cys
                85                  90                  95 tac ttt att tct act gtg aag agg agc tgg act tca gcc caa aat gct     336
Tyr Phe Ile Ser Thr Val Lys Arg Ser Trp Thr Ser Ala Gln Asn Ala
            100                 105                 110 tgt tct gaa cat ggt gct act ctt gct gtc att gat tct gaa aag gac     384
Cys Ser Glu His Gly Ala Thr Leu Ala Val Ile Asp Ser Glu Lys Asp
        115                 120                 125 atg aac ttt cta aaa cga tac gca ggt aga gag gaa cac tgg gtt gga     432
Met Asn Phe Leu Lys Arg Tyr Ala Gly Arg Glu Glu His Trp Val Gly
    130                 135                 140 ctg aaa aag gaa cct ggt cac cca tgg aag tgg tca aat ggc aaa gaa     480
Leu Lys Lys Glu Pro Gly His Pro Trp Lys Trp Ser Asn Gly Lys Glu
145                 150                 155                 160 ttt aac aac tgg ttc aac gtt aca ggg tct gac aag tgt gtt ttt ctg     528
Phe Asn Asn Trp Phe Asn Val Thr Gly Ser Asp Lys Cys Val Phe Leu
                165                 170                 175 aaa aac aca gag gtc agc agc atg gaa tgt gag aag aat tta tac tgg     576
Lys Asn Thr Glu Val Ser Ser Met Glu Cys Glu Lys Asn Leu Tyr Trp
            180                 185                 190 ata tgt aac aaa cct tac aaa taa                                     600
Ile Cys Asn Lys Pro Tyr Lys
        195
```

<210> SEQ ID NO 30
<211> LENGTH: 199
<212> TYPE: PRT
<213> ORGANISM: Homo sapiens

<400> SEQUENCE: 30

Met Ser Ser Glu Asn Cys Phe Val Ala Glu Asn Ser Ser Leu His Pro
1               5                   10                  15

Glu Ser Gly Gln Glu Asn Asp Ala Thr Ser Pro His Phe Ser Thr Arg
            20                  25                  30

```
His Glu Gly Ser Phe Gln Val Pro Val Leu Cys Ala Val Met Asn Val
         35                  40                  45

Val Phe Ile Thr Ile Leu Ile Ile Ala Leu Ile Ala Leu Ser Val Gly
 50                  55                  60

Gln Tyr Asn Cys Pro Gly Gln Tyr Thr Phe Ser Met Pro Ser Asp Ser
 65                  70                  75                  80

His Val Ser Ser Cys Ser Glu Asp Trp Val Gly Tyr Gln Arg Lys Cys
                 85                  90                  95

Tyr Phe Ile Ser Thr Val Lys Arg Ser Trp Thr Ser Ala Gln Asn Ala
            100                 105                 110

Cys Ser Glu His Gly Ala Thr Leu Ala Val Ile Asp Ser Glu Lys Asp
            115                 120                 125

Met Asn Phe Leu Lys Arg Tyr Ala Gly Arg Glu Glu His Trp Val Gly
130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Gly Lys Asn Leu Tyr Trp
            180                 185                 190

Ile Cys Asn Lys Pro Tyr Lys
            195

<210> SEQ ID NO 31
<211> LENGTH: 600
<212> TYPE: DNA
<213> ORGANISM: Mus musculus
<220> FEATURE:
<221> NAME/KEY: CDS
<222> LOCATION: (1)..(600)

<400> SEQUENCE: 31 atg gat tct gaa aac tgt tct ata acg gaa aat agc tct tca cat ctg      48
Met Asp Ser Glu Asn Cys Ser Ile Thr Glu Asn Ser Ser Ser His Leu
1               5                   10                  15 gag aga ggg cag aag gac cat ggc acc agt ata cat ttt gag aag cat      96
Glu Arg Gly Gln Lys Asp His Gly Thr Ser Ile His Phe Glu Lys His
                20                  25                  30 cat gaa gga tcc att caa gtt tct atc cct tgg gct gtg tta ata gtg     144
His Glu Gly Ser Ile Gln Val Ser Ile Pro Trp Ala Val Leu Ile Val
         35                  40                  45 gtc ctc atc acg tcc tta ata ata gct ctc att gcc tta aat gtg ggc     192
Val Leu Ile Thr Ser Leu Ile Ile Ala Leu Ile Ala Leu Asn Val Gly
 50                  55                  60 aag tac aat tgc cca ggc ttg tac gag aag ttg gaa tca tct gac cac     240
Lys Tyr Asn Cys Pro Gly Leu Tyr Glu Lys Leu Glu Ser Ser Asp His
 65                  70                  75                  80 cat gtt gct acc tgc aag aat gag tgg att tca tac aag agg aca tgt     288
His Val Ala Thr Cys Lys Asn Glu Trp Ile Ser Tyr Lys Arg Thr Cys
                 85                  90                  95 tac ttc ttc tcc acc aca acc aag agt tgg gcc ttg gcc caa cgc tct     336
Tyr Phe Phe Ser Thr Thr Thr Lys Ser Trp Ala Leu Ala Gln Arg Ser
            100                 105                 110 tgt tct gaa gat gct gct act ctt gct gta att gat tca gaa aag gac     384
Cys Ser Glu Asp Ala Ala Thr Leu Ala Val Ile Asp Ser Glu Lys Asp
            115                 120                 125 atg acg ttt ctg aag cga tat tct ggt gaa ctg gaa cat tgg att ggg     432
Met Thr Phe Leu Lys Arg Tyr Ser Gly Glu Leu Glu His Trp Ile Gly
```

-continued

```
                 130                 135                 140
ctg aaa aat gaa gct aat cag aca tgg aaa tgg gca aat ggc aaa gaa       480
Leu Lys Asn Glu Ala Asn Gln Thr Trp Lys Trp Ala Asn Gly Lys Glu
145                 150                 155                 160 ttt aac agc tgg ttc aac ttg acg ggg tct ggg agg tgc gtg tcc gtg       528
Phe Asn Ser Trp Phe Asn Leu Thr Gly Ser Gly Arg Cys Val Ser Val
                165                 170                 175 aac cac aaa aat gtt acc gct gtg gac tgt gag gca aac ttc cac tgg       576
Asn His Lys Asn Val Thr Ala Val Asp Cys Glu Ala Asn Phe His Trp
            180                 185                 190 gtc tgc agc aag ccc tcc aga tga                                       600
Val Cys Ser Lys Pro Ser Arg
        195
```

<210> SEQ ID NO 32
<211> LENGTH: 199
<212> TYPE: PRT
<213> ORGANISM: Mus musculus

<400> SEQUENCE: 32

```
Met Asp Ser Glu Asn Cys Ser Ile Thr Glu Asn Ser Ser His Leu
1               5                   10                  15

Glu Arg Gly Gln Lys Asp His Gly Thr Ser Ile His Phe Glu Lys His
                20                  25                  30

His Glu Gly Ser Ile Gln Val Ser Ile Pro Trp Ala Val Leu Ile Val
            35                  40                  45

Val Leu Ile Thr Ser Leu Ile Ile Ala Leu Ile Ala Leu Asn Val Gly
        50                  55                  60

Lys Tyr Asn Cys Pro Gly Leu Tyr Glu Lys Leu Glu Ser Ser Asp His
65                  70                  75                  80

His Val Ala Thr Cys Lys Asn Glu Trp Ile Ser Tyr Lys Arg Thr Cys
                85                  90                  95

Tyr Phe Phe Ser Thr Thr Thr Lys Ser Trp Ala Leu Ala Gln Arg Ser
                100                 105                 110

Cys Ser Glu Asp Ala Ala Thr Leu Ala Val Ile Asp Ser Glu Lys Asp
            115                 120                 125

Met Thr Phe Leu Lys Arg Tyr Ser Gly Glu Leu Glu His Trp Ile Gly
        130                 135                 140

Leu Lys Asn Glu Ala Asn Gln Thr Trp Lys Trp Ala Asn Gly Lys Glu
145                 150                 155                 160

Phe Asn Ser Trp Phe Asn Leu Thr Gly Ser Gly Arg Cys Val Ser Val
                165                 170                 175

Asn His Lys Asn Val Thr Ala Val Asp Cys Glu Ala Asn Phe His Trp
            180                 185                 190

Val Cys Ser Lys Pro Ser Arg
        195
```

<210> SEQ ID NO 33
<211> LENGTH: 5
<212> TYPE: PRT
<213> ORGANISM: Artificial Sequence
<220> FEATURE:
<223> OTHER INFORMATION: Synthetic human CD69 partial peptide

<400> SEQUENCE: 33

```
Tyr Asn Cys Pro Gly
1               5
```

```
<210> SEQ ID NO 34
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 34

Ala Leu Ser Val Gly Gln Tyr Asn Cys Pro Gly Gln
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 35

Val Gly Gln Tyr Asn Cys Pro Gly Gln Tyr Thr Phe
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 36

Tyr Asn Cys Pro Gly Gln Tyr Thr Phe Ser Met Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 37

Pro Gly Gln Tyr Thr Phe Ser Met Pro Ser Asp Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 38

Tyr Thr Phe Ser Met Pro Ser Asp Ser His Val Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 39

Ser Met Pro Ser Asp Ser His Val Ser Ser Cys Ser
1               5                   10

<210> SEQ ID NO 40
```

```
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 40

Ser Asp Ser His Val Ser Ser Cys Ser Glu Asp Trp
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 41

His Val Ser Ser Cys Ser Glu Asp Trp Val Gly Tyr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 42

Ser Cys Ser Glu Asp Trp Val Gly Tyr Gln Arg Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 43

Glu Asp Trp Val Gly Tyr Gln Arg Lys Cys Tyr Phe
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 44

Val Gly Tyr Gln Arg Lys Cys Tyr Phe Ile Ser Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 45

Gln Arg Lys Cys Tyr Phe Ile Ser Thr Val Lys Arg
1               5                   10

<210> SEQ ID NO 46
<211> LENGTH: 12
```

```
<212> TYPE: PRT
<213> ORGANISM: Artificial Sequence
<220> FEATURE:
<223> OTHER INFORMATION: Synthetic human CD69 partial peptide

<400> SEQUENCE: 46

Cys Tyr Phe Ile Ser Thr Val Lys Arg Ser Trp Thr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 47

Ile Ser Thr Val Lys Arg Ser Trp Thr Ser Ala Gln
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 48

Val Lys Arg Ser Trp Thr Ser Ala Gln Asn Ala Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 49

Ser Trp Thr Ser Ala Gln Asn Ala Cys Ser Glu His
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 50

Ser Ala Gln Asn Ala Cys Ser Glu His Gly Ala Thr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 51

Asn Ala Cys Ser Glu His Gly Ala Thr Leu Ala Val
1               5                   10

<210> SEQ ID NO 52
<211> LENGTH: 12
<212> TYPE: PRT
```

<213> ORGANISM: Artificial Sequence
<220> FEATURE:
<223> OTHER INFORMATION: Synthetic human CD69 partial peptide

<400> SEQUENCE: 52

Ser Glu His Gly Ala Thr Leu Ala Val Ile Asp Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 53

Gly Ala Thr Leu Ala Val Ile Asp Ser Glu Lys Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 54

Leu Ala Val Ile Asp Ser Glu Lys Asp Met Asn Phe
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 55

Ile Asp Ser Glu Lys Asp Met Asn Phe Leu Lys Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 56

Glu Lys Asp Met Asn Phe Leu Lys Arg Tyr Ala Gly
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 57

Met Asn Phe Leu Lys Arg Tyr Ala Gly Arg Glu Glu
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 58

Leu Lys Arg Tyr Ala Gly Arg Glu Glu His Trp Val
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 59

Tyr Ala Gly Arg Glu Glu His Trp Val Gly Leu Lys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 60

Arg Glu Glu His Trp Val Gly Leu Lys Lys Glu Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 61

His Trp Val Gly Leu Lys Lys Glu Pro Gly His Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 62

Gly Leu Lys Lys Glu Pro Gly His Pro Trp Lys Trp
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 63

Lys Glu Pro Gly His Pro Trp Lys Trp Ser Asn Gly
1               5                   10

<210> SEQ ID NO 64
<211> LENGTH: 12
<212> TYPE: PRT
<213> ORGANISM: Artificial Sequence
<220> FEATURE:

<223> OTHER INFORMATION: Synthetic human CD69 partial peptide

<400> SEQUENCE: 64

Gly His Pro Trp Lys Trp Ser Asn Gly Lys Glu Phe
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 65

Trp Lys Trp Ser Asn Gly Lys Glu Phe Asn Asn Trp
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 66

Ser Asn Gly Lys Glu Phe Asn Asn Trp Phe Asn Val
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 67

Lys Glu Phe Asn Asn Trp Phe Asn Val Thr Gly Ser
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 68

Asn Asn Trp Phe Asn Val Thr Gly Ser Asp Lys Cys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 69

Phe Asn Val Thr Gly Ser Asp Lys Cys Val Phe Leu
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic human CD69 partial peptide

```
<400> SEQUENCE: 70

Thr Gly Ser Asp Lys Cys Val Phe Leu Lys Asn Thr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 71

Asp Lys Cys Val Phe Leu Lys Asn Thr Glu Val Ser
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 72

Val Phe Leu Lys Asn Thr Glu Val Ser Ser Met Glu
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 73

Lys Asn Thr Glu Val Ser Ser Met Glu Cys Glu Lys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 74

Glu Val Ser Ser Met Glu Cys Glu Lys Asn Leu Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 75

Ser Met Glu Cys Glu Lys Asn Leu Tyr Trp Ile Cys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic human CD69 partial peptide
```

```
<400> SEQUENCE: 76

Cys Glu Lys Asn Leu Tyr Trp Ile Cys Asn Lys Pro
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic human CD69 partial peptide

<400> SEQUENCE: 77

Lys Asn Leu Tyr Trp Ile Cys Asn Lys Pro Tyr Lys
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Synthetic human CD69 partial peptide

<400> SEQUENCE: 78

Tyr Ala Gly Arg Glu Glu
1               5
```